(12) United States Patent
Hayakawa et al.

(10) Patent No.: US 12,043,534 B2
(45) Date of Patent: Jul. 23, 2024

(54) ASEPTIC FILLING METHOD AND ASEPTIC FILLING MACHINE

(71) Applicant: Dai Nippon Printing Co., Ltd., Tokyo (JP)

(72) Inventors: Atsushi Hayakawa, Tokyo (JP); Yoshinori Sato, Tokyo (JP); Seiji Kuwano, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 148 days.

(21) Appl. No.: 17/815,663

(22) Filed: Jul. 28, 2022

(65) Prior Publication Data

US 2022/0371873 A1 Nov. 24, 2022

Related U.S. Application Data

(63) Continuation of application No. PCT/JP2021/008192, filed on Mar. 3, 2021.

(30) Foreign Application Priority Data

Mar. 13, 2020 (JP) .................................. 2020-044042

(51) Int. Cl.
*B67C 7/00* (2006.01)
*A61L 2/18* (2006.01)
(Continued)

(52) U.S. Cl.
CPC ............ *B67C 7/0073* (2013.01); *A61L 2/186* (2013.01); *A61L 2/208* (2013.01);
(Continued)

(58) Field of Classification Search
CPC ........... B65B 3/04; B65B 55/10; B65B 3/022; B65B 55/103; B65B 55/06; B67C 7/0073;
(Continued)

(56) References Cited

U.S. PATENT DOCUMENTS

2011/0094616 A1* 4/2011 Hayakawa .............. B65B 55/10
141/85

FOREIGN PATENT DOCUMENTS

JP S57-195610 A 12/1982
JP 2006-111295 A 4/2006
(Continued)

OTHER PUBLICATIONS

International Search Report and Written Opinion (Application No. PCT/JP2021/008192) dated May 11, 2021 (with English translation).

*Primary Examiner* — Jacob A Smith
(74) *Attorney, Agent, or Firm* — BURR PATENT LAW, PLLC

(57) ABSTRACT

Even when the filling speed increases, the surface temperature of a molded bottle falls within a constant range, and a sterilizer adequately sterilizes the bottle.
A preform is heated, the heated preform is sealed in a mold, the preform sealed in the mold is blow-molded into a bottle, the surface temperatures of a neck portion, a body portion, and a bottom portion of the molded bottle are measured, and the mold temperatures of a neck portion, a body portion, and a bottom portion of the mold is so adjusted that the measured surface temperature of the bottle falls within a specified temperature range.

6 Claims, 11 Drawing Sheets

(51) Int. Cl.
*A61L 2/20* (2006.01)
*B29C 49/48* (2006.01)
*B29C 49/78* (2006.01)
*B67C 3/22* (2006.01)
*B29L 31/00* (2006.01)

(52) U.S. Cl.
CPC ........ *B29C 49/4823* (2013.01); *B29C 49/786* (2013.01); *B67C 3/22* (2013.01); *B67C 7/002* (2013.01); *A61L 2202/15* (2013.01); *A61L 2202/23* (2013.01); *B29C 2049/4846* (2013.01); *B29C 2049/78645* (2022.05); *B29L 2031/7158* (2013.01); *B67C 2003/227* (2013.01); *B67C 2007/006* (2013.01); *B67C 2007/0066* (2013.01)

(58) Field of Classification Search
CPC .............. B67C 7/002; B67C 2003/227; B67C 2003/228; B67C 3/242
USPC .................................. 53/426, 126, 452, 425
See application file for complete search history.

(56) References Cited

FOREIGN PATENT DOCUMENTS

| | | | |
|---|---|---|---|
| JP | 2008-155401 A | 7/2008 | |
| JP | 2009-280222 A | 12/2009 | |
| JP | 2009280222 A | * 12/2009 | ............... B29C 1/00 |
| JP | 2010-155631 A | 7/2010 | |

* cited by examiner

FIG. 2(A) SUPPLY PREFORM

FIG. 2 (B) HEAT PREFORM

FIG. 2 (C) BLOW-MOLD

FIG. 2(D) TAKE OUT BOTTLE

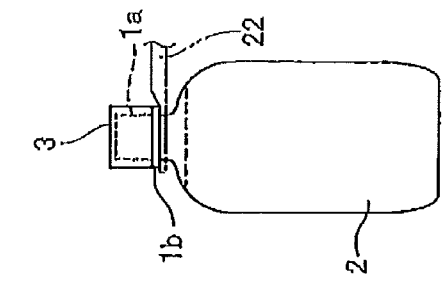
FIG. 3 (H)
SEAL
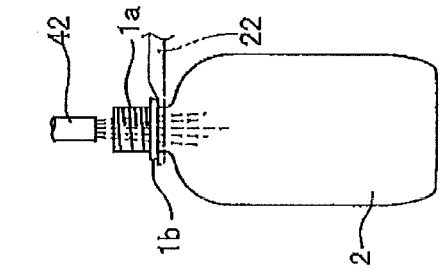
FIG. 3(G)
FILL
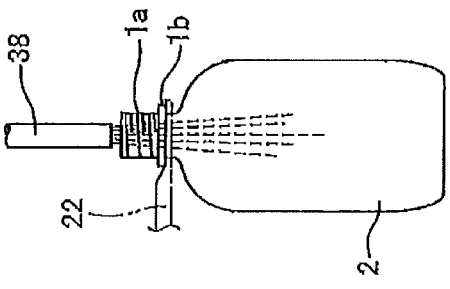
FIG. 3 (F-1)
AIR-RINSE
FIG. 3 (F-2)
AIR-RINSE
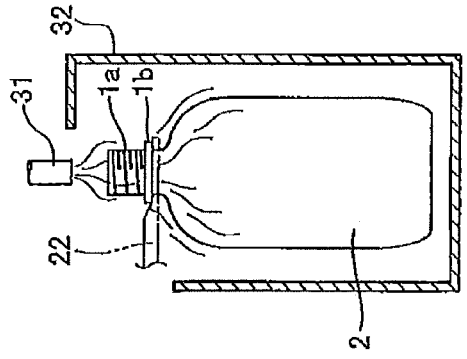
FIG. 3 (E-1)
BLAST STERILIZER GAS
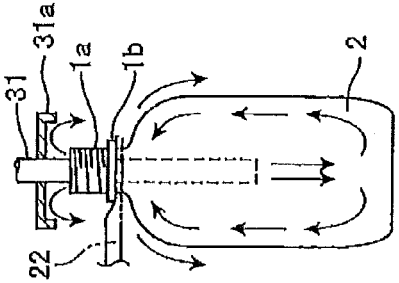
FIG. 3 (E-2)
BLAST STERILIZER GAS

ASEPTIC FILLING METHOD AND ASEPTIC FILLING MACHINE

TECHNICAL FIELD

The present invention relates to sterilized filling involving molding a preform into a bottle, sterilizing the molded bottle with a sterilizer, filling the sterilized bottle with a sterilized content, and sealing the bottle filled with the content with a sterilized lid member, and in particular to an aseptic filling method and an aseptic filling machine that measure the surface temperature of the bottle to be molded at the start of the molding operation or the surface temperature of the mold that molds the bottle, and control the temperature of the mold that molds the bottle.

BACKGROUND ART

There is a known aseptic filling machine that includes a molding portion that blow-molds a preform into a bottle, a sterilizing portion that sterilizes the bottle molded by the molding portion with a sterilizer, an air-rinsing portion that air-rinses the bottle sterilized in the sterilizing portion, and a filling portion that fills the bottle air-rinsed in the air-rinsing portion with a content and seals the bottle, the portions being connected to each other, a transfer device being provided for continuously transferring the bottle from the molding portion to the filling portion via the sterilizing portion and the air-rinsing portion, and the part from the molding portion to the filling portion being covered with a chamber. With this aseptic filling machine, the heat applied to the bottle in the molding phase can be used to increase the sterilization effect of a mist of hydrogen peroxide, which is used as the sterilizer (see Patent Literature 1).

There is another known aseptic filling machine that inspects the surface temperature of bottles molded from preforms, conveys only the bottles the surface temperature of which is ascertained to be equal to or higher than a certain temperature to a sterilizing portion and removes any bottle the surface temperature of which is lower than the certain temperature (see Patent Literature 2).

CITATION LIST

Patent Literature

Patent Literature 1: Japanese Patent Laid-Open No. 2006-111295
Patent Literature 2: Japanese Patent Laid-Open No. 2010-155631

SUMMARY OF INVENTION

Technical Problem

With conventional aseptic filling machines, molding of bottles, sterilization of the bottles with a sterilizer, and filling the bottles with a drink can be continuously performed. However, all the molded bottles are fed to the sterilization step and the filling step, and therefore, there is a risk that a faulty bottle may be filled with a drink and shipped. For example, if a bottle insufficiently heated is fed to the sterilization step, there is a risk that the sterilization may be inadequate, and that such a bottle may be filled with a drink and shipped.

In view of this, in Patent Literature 2, the surface temperature of the molded bottles is measured, and only the bottles the surface temperature of which is equal to or higher than a certain temperature are conveyed to the sterilizing portion. The surface temperature of the molded bottles depends on the temperature of the mold that molds the bottles. The mold temperature is, however, so set that the surface temperature of bottles molded after the preform-to-bottle molding has reached a stable state is higher than or equal to the certain temperature. Immediately after the start of the operation of molding preforms into bottles, the mold has not received the heat from the heated preforms, so that the surface temperature of the bottles to be molded has not reached the certain temperature in some cases.

In view of this, the temperature of the mold is raised at the start of the molding to allow the mold to receive the heat from the heated preforms when the state of the molding reaches the stable state, so that the temperature of the mold undesirably rises beyond the temperature set at the start of the molding, resulting in molding failure, such as bleaching and uneven walls of the molded bottles.

To avoid such molding failure, the temperature of the mold is so set that the surface temperature of the bottles after a certain period elapses from the start of the molding and when the surface temperature of the bottles reaches a stable state fall within a specified temperature range. Therefore, at the start of the bottle molding operation, the surface temperature of the bottles to be molded may fall below the specified range. Since the removal of the bottles having surface temperatures that do not fall within the specified temperature range results in wasted bottles, a large amount of sterilizer is caused to come into contact with the bottles to sterilize the bottles having surface temperatures that do not fall within the specified temperature range. The amount of sterilizer becomes excessive when the surface temperature of the bottles reaches the stable state after the certain period elapses from the start of the molding, resulting in an increase in the amount of sterilizer left on the bottles.

There is therefore a demand for an aseptic filling machine that produces bottles having surface temperatures that fall within a certain temperature range even after a certain period elapses from the start of the operation of molding preforms into the bottles, and adequately sterilizes the bottles with a small amount of sterilizer from the start of the molding.

An object of the present invention is to provide an aseptic filling method and an aseptic filling machine that can solve the problems described above.

Solution to Problem

To solve the problems described above, the present invention is configured as follows.

An aseptic filling method according to the present invention includes heating a preform and sealing the heated preform in a mold formed of a neck portion, a body portion, and a bottom portion, blow-molding the preform sealed in the mold into a bottle, measuring a surface temperature of at least the body portion out of surface temperatures of the neck portion, the body portion, and the bottom portion of the molded bottle, controlling a temperature of a mold temperature adjusting medium circulated through the mold to control mold temperatures of the neck portion, the body portion, and the bottom portion of the mold in such a way that the measured surface temperature of the bottle falls within a specified temperature range, causing a gas or mist of a sterilizer or a mixture thereof to come into contact with the molded bottle, sterilizing a surface of the bottle, filling the sterilized bottle with a sterilized content, and sealing the bottle filled with the content with a sterilized lid member.

In the aseptic filling method according to the present invention, it is preferable that when the blow molding is started, the temperature of the mold temperature adjusting medium is set to a high temperature that is higher than the temperature of the mold temperature adjusting medium after the blow molding is started and a certain period elapses, and the temperature of the mold temperature adjusting medium circulated through the mold is so controlled that the surface temperature of the bottle measured immediately after the blow molding is started is approximately to the surface temperature of the bottle measured after the certain period.

In the aseptic filling method according to the present invention, it is preferable that let t1° C. be the surface temperature of the body portion of the bottle at the start of the blow molding, and t2° C. be the surface temperature of the body portion of the bottle after the blow molding is started and a specified period elapses, the temperature of the mold temperature adjusting medium circulated through the body portion mold is raised by $\Delta t°$ C., which is a difference between t2 and t1, followed by the blow molding of the bottle, when the surface temperature of the body portion of the bottle at the start of the blow molding is t3° C., the difference $\Delta t'°$ C. between t2 and t3 is fed back to control the temperature of the mold temperature adjusting medium, the temperature of the mold temperature adjusting medium circulated through the body portion mold is raised by $\Delta t'°$ C., followed by the blow molding of the bottle, and the above operation is repeated to determine $(\Delta t + \Delta t' \ldots )°$ C., which allows t1 and t2 to be equal to each other and which is defined as the high temperature.

An aseptic filling method according to the present invention includes heating a preform, sealing the heated preform in a mold formed of a neck portion, a body portion, and a bottom portion, blow-molding the preform sealed in the mold into a bottle, measuring a surface temperature of at least the body portion out of surface temperatures of the neck portion, the body portion, and the bottom portion of the mold, controlling a temperature of a mold temperature adjusting medium circulated through the mold to control mold temperatures of the neck portion, the body portion, and the bottom portion of the mold in such a way that the measured surface temperature falls within a specified temperature range, causing a gas or mist of a sterilizer or a mixture thereof to come into contact with the bottle molded by the mold having the adjusted mold temperatures, sterilizing a surface of the bottle and filling the sterilized bottle with a sterilized content and sealing the bottle filled with the content with a sterilized lid member.

In the aseptic filling method according to the present invention, it is preferable that when the blow molding is started, the temperature of the mold temperature adjusting medium is set to a high temperature that is higher than the temperature of the mold temperature adjusting medium after the blow molding is started and a certain period elapses, and the temperature of the mold temperature adjusting medium circulated through the mold is so controlled that the surface temperature of the mold measured immediately after the blow molding is started is approximately to the surface temperature of the mold measured after the certain period.

An aseptic filling machine according to the present invention includes a heating apparatus that heats a preform, a mold formed of a neck portion, a body portion, and a bottom portion that seal the preform to blow-mold the heated preform into a bottle, a blow-molding apparatus that blow-molds the preform sealed in the mold into the bottle, a bottle surface temperature measuring apparatus that measures a surface temperature of at least the body portion out of surface temperatures of the neck portion, the body portion, and the bottom portion of the blow-molded bottle, a mold temperature adjusting apparatus that includes a mold temperature adjusting medium controlling apparatus that controls a temperature of a mold temperature adjusting medium circulated through the mold formed of the neck portion, the body portion, and the bottom portion and adjusts a temperature of the mold formed of the neck portion, the body portion, and the bottom portion, a bottle sterilizing apparatus that blasts a gas or mist of a sterilizer or a mixture thereof to the bottle to sterilize the bottle, a filling apparatus that fills the sterilized bottle with a sterilized content, a sealing apparatus that seals the bottle filled with the content with a sterilized lid member, and a conveying apparatus that conveys the preform or the bottle from the heating apparatus to the sealing apparatus.

In the aseptic filling machine according to the present invention, it is preferable that when the blow molding is started, the mold temperature adjusting medium controlling apparatus sets the temperature of the mold temperature adjusting medium to a high temperature that is higher than the temperature of the mold temperature adjusting medium after the blow molding is started and a certain period elapses, and controls the temperature of the mold temperature adjusting medium circulated through the mold in such a way that the surface temperature of the bottle measured immediately after the blow molding is started is approximately to the surface temperature of the bottle measured after the certain period.

In the aseptic filling machine according to the present invention, it is preferable that let t1° C. be the surface temperature of the body portion of the bottle at the start of the blow molding, and t2° C. be the surface temperature of the body portion of the bottle after the blow molding is started and a specified period elapses, the mold temperature adjusting medium controlling apparatus includes a computation apparatus that raises the temperature of the mold temperature adjusting medium circulated through the body portion mold by $\Delta t°$ C., which is a difference between t2 and t1, and performs the blow molding of the bottle, feeds back the difference $\Delta t'°$ C. between t2 and t3 to the mold temperature adjusting medium controlling apparatus when the surface temperature of the body portion of the bottle at the start of the blow molding is t3° C., raises the temperature of the mold temperature adjusting medium circulated through the body portion mold is by $\Delta t'°$ C., and performs the blow molding of the bottle, and repeats the above operation to compute the high temperature $(\Delta t + \Delta t' \ldots )°$ C., which allows t1 and t2 to be equal to each other.

An aseptic filling machine according to the present invention includes a heating apparatus that heats a preform, a mold formed of a neck portion, a body portion, and a bottom portion that seal the preform to blow-mold the heated preform into a bottle, a mold surface temperature measuring apparatus that measures a surface temperature of at least the body portion out of surface temperatures of the mold formed of the neck portion, the body portion, and the bottom portion, a mold temperature adjusting apparatus that includes a mold temperature adjusting medium controlling apparatus that controls a temperature of a mold temperature adjusting medium circulated through the mold formed of the neck portion, the body portion, and the bottom portion and adjusts a temperature of the mold formed of the neck portion, the body portion, and the bottom portion, a blow-molding apparatus that blow-molds the preform sealed in the mold into the bottle, a bottle sterilizing apparatus that blasts a gas or mist of a sterilizer or a mixture thereof to the bottle to sterilize the bottle, a filling apparatus that fills the sterilized bottle with a sterilized content, a sealing apparatus that seals the bottle filled with the content with a sterilized lid member, and a conveying apparatus that conveys the preform or the bottle from the heating apparatus to the sealing apparatus.

In the aseptic filling machine according to the present invention, it is preferable that when the blow molding is started, the mold temperature adjusting medium controlling apparatus sets the temperature of the mold temperature adjusting medium to a high temperature that is higher than the temperature of the mold temperature adjusting medium after the blow molding is started and a certain period elapses, and controls the temperature of the mold temperature adjusting medium circulated through the mold in such a way that the surface temperature of the mold measured immediately after the blow molding is started is approximately to the surface temperature of the mold measured after the certain period.

Advantageous Effects of Invention

The bottle sterilization effect is improved by blasting a gas or mist of a sterilizer or a mixture thereof to the inner and outer surfaces of a bottle produced by blow-molding a heated preform into contact with a sterilizer while the heat applied to the preform remains in the bottle. In order that adequate heat remains in the molded bottle, the temperature of the mold used for blow-molding the heated preform needs to fall within a specified temperature range. The preform is sealed in a mold formed by three molds corresponding to a neck portion, a body portion and a bottom portion of the bottle to be blow-molded, an extension rod is inserted into the preform, and high-pressure air is blasted to the preform. The surface of the bottle molded is shaped to conform to the shape of the neck portion mold, the body portion mold, and the bottom portion mold, and the surfaces of the molds are in contact with the outer surface of the bottle during the molding. Therefore, the temperature of the bottle to which the gas or mist of the sterilizer of the mixture thereof is blasted is determined by the temperature to which the preform is heated and the temperatures of the molds.

The present invention includes sealing a heated preform in a mold formed of a neck portion, a body portion, and a bottom portion, blow-molding the heated preform into a bottle, measuring the surface temperatures of the molded bottle, and adjusting the surface temperature of the mold in such a way that the measured surface temperature of the bottle falls within a specified temperature range. The present invention further includes measuring the surface temperature of the mold and adjusting the temperature of the mold in such a way that the surface temperature of the mold falls within a specified temperature range. The thus configured method allows production of a bottle having a surface temperature falling within the specified temperature range even after the operation of molding the preform into the bottle is started and a certain period elapses. There are therefore provided an aseptic filling method and an aseptic filling machine that allow reliable sterilization of a bottle by bringing a gas or mist of a sterilizer in an amount smaller than those in related art or a mixture thereof to come into contact with the bottle. Further, according to the present invention, reducing the amount of sterilizer allows reduction in the sterilizer left in the bottle.

BRIEF DESCRIPTION OF DRAWINGS

FIGS. 3(E-1)-3(H) show steps performed by a bottle sterilizing apparatus and a filling apparatus of the aseptic filling machine according to the embodiment of the present invention, FIG. 3(E-1) showing a sterilizer gas blasting step performed with a bottle being shielded with a tunnel, FIG. 3(E-2) showing a sterilizer gas blasting step performed by inserting a sterilizer gas blasting nozzle into the bottle, FIG. 3(F-1) showing an air-rinsing step with the bottle in an upright position, FIG. 3(F-2) showing an air-rinsing step with the bottle in an inverted position, FIG. 3(G) showing a filling step, and FIG. 3(H) showing a sealing step.

DESCRIPTION OF EMBODIMENT

In the following, embodiments of the present invention will be described with reference to the drawings.

First Embodiment

Figure 1:
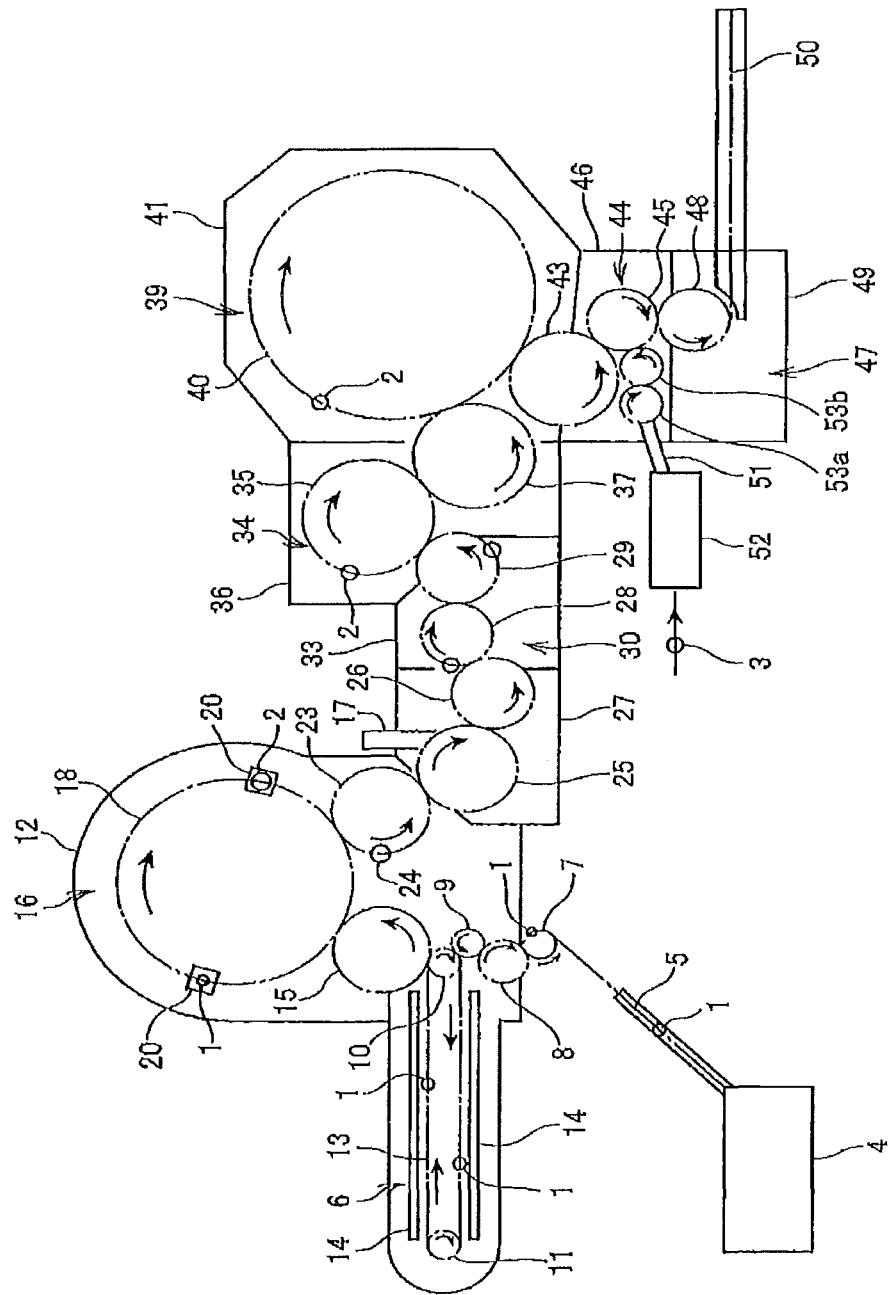
FIG. 1 is a plan view schematically showing an aseptic filling machine according to an embodiment of the present invention.

FIG. 1 shows an aseptic filling machine according to the present invention. An overview of the aseptic filling machine including a heating apparatus that heats a preform supplied, a blow-molding apparatus, a bottle surface temperature measuring apparatus, a bottle removing apparatus, a bottle sterilizing apparatus, a filling apparatus, and a sealing apparatus will be described with reference to FIG. 1. Steps performed by each of the apparatuses will then be described in detail with reference to FIGS. 2(A)-2(D), 3(E-1)-3(H) and 4. According to the first embodiment, when a preform is heated and molded into a bottle, the applied heat can be properly retained in the bottle and causes no deformation of the molded bottle.

As shown in FIG. 1, the aseptic filling machine according to the first embodiment includes a preform supplying apparatus 4, which supplies a preform 1, a heating apparatus 6, which heats the preform 1 to a temperature for molding the preform 1 into a bottle 2, a blow-molding apparatus 16, which molds the heated preform 1 into the bottle 2, a bottle surface temperature measuring apparatus 24, which measures the surface temperature of the blow-molded bottle 2, a bottle removing apparatus 17, which removes a blow-molded bottle 2 recognized to have a faulty appearance and a blow-molded bottle 2 the surface temperature of which does not fall within a specified temperature range, a bottle sterilizing apparatus 30, which sterilizes the bottle 2, an air-rinsing apparatus 34, which air-rinses the sterilized bottle 2, a filling apparatus 39, which fills the air-rinsed bottle 2 with a sterilized content, a lid member sterilizing apparatus 52, which sterilizes a lid member 3, which is a sealing member, a sealing apparatus 44, which seals the bottle 2 filled with the content with the sterilized lid member 3, and a discharging apparatus 47, which discharges the sealed bottle 2 out of the aseptic filling machine.

The aseptic filling machine includes a conveying apparatus that conveys the preform 1 or the bottle 2 from the heating apparatus 6 to the sealing apparatus 44.

The heating apparatus 6, which heats the preforms 1, the blow-molding apparatus 16, and the bottle surface temperature measuring apparatus 24 are shielded by a molding portion chamber 12, the bottle sterilizing apparatus 30 is shielded by a sterilizing portion chamber 33, the air-rinsing apparatus 34 is shielded by an air-rinsing portion chamber 36, the filling apparatus 39 is shielded by a filling portion chamber 41, the sealing apparatus 44 is shielded by a sealing portion chamber 46, and the discharging apparatus 47 and a discharging conveyor 50 are shielded by a discharging portion chamber 49. An atmosphere separation chamber 27 is provided between the blow-molding apparatus 16 and the bottle sterilizing apparatus 30 to prevent a gas or mist of a sterilizer or a mixture thereof produced in the bottle sterilizing apparatus 30 from flowing into the blow-molding apparatus 16. By venting the atmosphere separation chamber 27, the gas or mist of a sterilizer or a mixture thereof produced in the bottle sterilizing apparatus 30 is prevented from flowing into the blow-molding apparatus 16. The filling apparatus 39 and the sealing apparatus 44 may be shielded by a single chamber. Further, the lid member sterilizing apparatus 52 and the sealing apparatus 44 may be shielded by the single chamber. Further, the sealing apparatus 44 and the discharging apparatus 47 may also be shielded by the single chamber.

In operation of the aseptic filling machine, aseptic air, which is made aseptic by an aseptic filter, is supplied into the sterilizing portion chamber 33, the air-rinsing portion chamber 36, the filling portion chamber 41, the sealing portion chamber 46 and the discharging portion chamber 49. By supplying the aseptic air, the interior of each of the chambers is kept at a positive pressure, and the aseptic condition of the aseptic filling machine is maintained. The positive pressure is the highest in the filling portion chamber 41. The more upstream the chamber is located, such as the air-rinsing portion chamber 36 and the sterilizing portion chamber 33, the lower the positive pressure is set, and the more downstream the chamber is located, such as the sealing portion chamber 46 and the discharging portion chamber 49, the lower the positive pressure is set. The pressure in the atmosphere separation chamber 27 is substantially kept at the atmospheric pressure by venting the atmosphere separation chamber 27. For example, provided that the pressure in the filling portion chamber 41 ranges from 20 Pa to 40 Pa, the pressures in the other chambers are lower than the pressure in the filling portion chamber 41.

A description will be made of an aseptic filling method using the aseptic filling machine described above, the method including heating the preform 1 with the heating apparatus 6, sealing the heated preform 1 in a mold 20 provided in the blow-molding apparatus 16 and having a neck portion, a body portion, and a bottom portion, blow-molding the preform 1 sealed in the mold 20 into the bottle 2, measuring the surface temperature of at least one of a neck portion 2a, a body portion 2b, and a bottom portion 2c of the molded bottle 2, that is, the surface temperature of the body portion 2b, with the bottle surface temperature measuring apparatus 24, adjusting the mold temperatures of the neck portion, the body portion, and the bottom portion of the mold 20 with a mold temperature adjusting apparatus 54 in such a way that the surface temperature of the bottle 2 under measurement falls within a specified temperature range, bringing the gas or mist of the sterilizer or the mixture thereof to come into contact with the molded bottle 2 with the bottle sterilizing apparatus 30 to sterilize the surface of the bottle 2, filling the sterilized bottle 2 with a sterilized content with the filling apparatus 39, and sealing the bottle 2 filled with the content with sterilized lid member 3 with the sealing apparatus 44.

Figure 2:
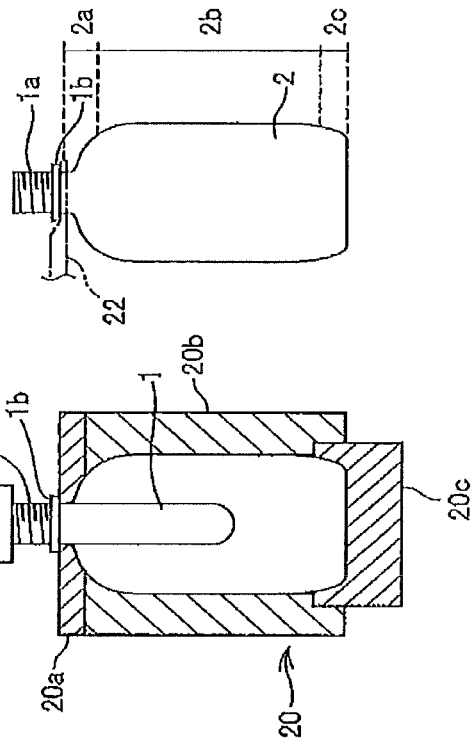
FIGS. 2(A)-2(D) show steps performed by a heating apparatus and a blow-molding apparatus of the aseptic filling machine according to the embodiment of the present invention, FIG. 2(A) showing a preform supplying step, FIG. 2(B) showing a preform heating step, FIG. 2(C) showing a blow-molding step, and FIG. 2(D) showing a bottle take out step.

In the aseptic filling machine, the preform 1 is heated, the heated preform 1 is sealed in the mold 20, which has a neck portion mold 20a, a body portion mold 20b, and a bottom portion mold 20c, the preform 1 sealed in the mold 20 is blow-molded into the bottle 2, the surface temperature of at least the body portion 2b is measured out of the neck portion 2a, the body portion 2b, and the bottom portion 2c of the molded bottle 2, and any bottle 2 the measured surface temperature of which does not fall within the specified temperature range is removed. The surface temperature is measured only at the body portion 2b in the description, and may be measured at two or three locations of the bottle 2. A bottle 2 to be molded but having a faulty appearance is also removed. The aseptic filling machine includes the bottle removing apparatus 17, which removes a bottle 2. Although the bottle removing apparatus 17 is provided in the atmosphere separation chamber 27 in FIG. 1, the bottle removing apparatus 17 can be provided at any location where the bottle is not sterilized yet. Any bottle 2 having been molded with the neck portion 2a, the body portion 2b, and the bottom portion 2c each of which has a temperature that falls within the specified temperature range and having been recognized to have no faulty appearance is sterilized by the gas or mist of the sterilizer of the mixture thereof blasted to the bottle 2. FIG. 2(D) shows the ranges of the neck portion 2a, the body portion 2b, and the bottom portion 2c of the bottle 2.

Preforms such as the preform 1 shown in FIG. 2(A) are successively conveyed from the preform supplying apparatus 4 shown in FIG. 1 to the heating apparatus 6 at a desired speed by a preform supply conveyor 5.

The preform 1 according to the first embodiment is a bottomed cylindrical body having a test tube shape, and is provided with a mouth portion 1a like that of the bottle 2 shown in FIG. 2(D) in an early stage of the molding of the preform 1. A male thread is formed on the mouth portion 1a at the same time as the molding of the preform 1. Further, a support ring 1b used for conveyance is formed on the preform 1 below the mouth portion 1a. The preform 1 or the bottle 2 travels in the aseptic filling machine with the support ring 1b gripped by a gripper 22. The preform 1 is molded by injection molding, compression molding, or the like. The preform 1 is made of a thermoplastic resin, such as polyethylene terephthalate, polyethylene naphthalate, polypropylene or polyethylene, may be made of any of the resins described above or a mixture thereof, and may contain a recycled thermoplastic resin. Further, to provide a barrier property, the preform 1 may include a layer of a thermoplastic resin, such as ethylene-vinyl alcohol copolymer or polyamide having metaxylylene diamine or other aromatic amine as a monomer, or may contain a mixture of the materials described above.

The preform 1 supplied to the heating apparatus 6 is conveyed by wheels 7 and 8, on which a large number of grippers 22 are provided at regular intervals and reaches a heating apparatus conveying wheel 9. At the heating apparatus conveying wheel 9, the preform 1 is released from the gripper 22 as shown in FIG. 2(B) and conveyed with a spindle 19 inserted into the mouth portion 1a of the preform 1.

As shown in FIG. 2(B), the preform 1 is heated to a temperature suitable for the subsequent blow molding by an infrared heater 14 or any other heating device. The temperature preferably ranges from 90° C. to 130° C.

The temperature of the mouth portion 1a of the preform 1 is kept lower than or equal to 70° C. to prevent deformation or the like of the mouth portion 1a.

As shown in FIG. 2(B), the preform 1 is conveyed by an endless chain 13 while being heated by the infrared heater 14 and rotated with the spindle 19 inserted into the mouth portion 1a. The spindles 19 are provided at regular intervals on the endless chain 13. The endless chain 13 rotates on pulleys 10 and 11. Instead of the spindle 19, a mandrel may be inserted into the preform 1 to rotate and convey the preform 1 in the inverted position.

The heated preform 1 is released from the spindle 19, gripped by the gripper 22, and conveyed to a molding wheel 18 in the blow-molding apparatus 16 via a wheel 15. As shown in FIG. 2(C), in the mold 20 provided on the molding wheel 18, the preform 1 is blow-molded into the bottle 2. The mold 20 has the neck portion mold 20a, the body portion mold 20b and the bottom portion mold 20c. The neck portion mold 20a and the body portion mold 20b are split molds and typically formed of a pair of two parts. The bottom portion mold 20c is typically formed of one piece. A plurality of molds 20 and a plurality of blow nozzles 21 are arranged around the molding wheel 18, and rotate around the molding wheel 18 at a certain speed as the molding wheel 18 rotates.

When the heated preform 1 arrives, the mold 20 holds and seals the preform 1. After that, the blow nozzle 21 is joined to the preform 1, and an extension rod that is not shown is introduced into a hole provided in the blow nozzle 21 and inserted into the preform 1. The preform 1 is stretched lengthwise by the inserted extension rod, and at the same time is stretched crosswise by a gas, such as high-pressure air, blasted to the preform 1 via the blow nozzle 21. The preform 1 is thus molded into the bottle 2 in the mold 20. As shown in FIG. 2(D), the mold 20 is then opened, and the molded bottle 2 is took out from the mold 20, gripped at the support ring 1b by the gripper 22 provided on an inspection wheel 23 and passed to the inspection wheel 23.

Figure 5:
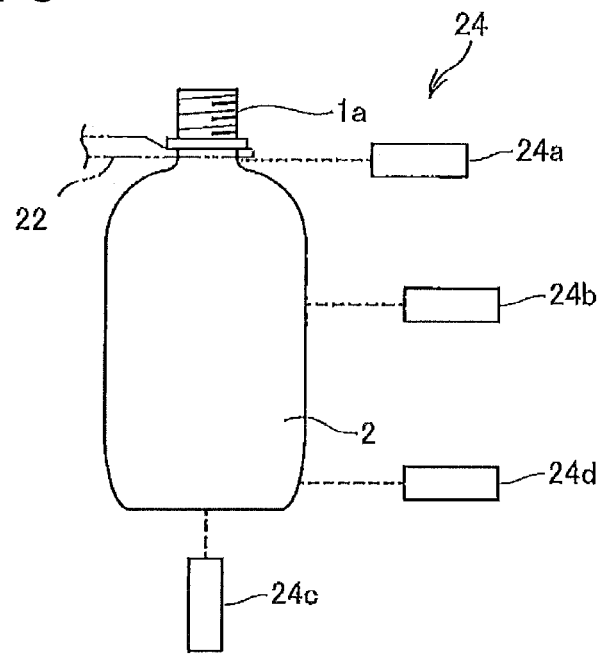
FIG. 5 shows a bottle surface temperature measuring apparatus provided in the aseptic filling machine according to the embodiment of the present invention.

The inspection wheel 23 is provided with the bottle surface temperature measuring apparatus 24, which measures the surface temperatures of the neck portion 2a, the body portion 2b, and the bottom portion 2c of the molded bottle 2. The bottle surface temperature measuring apparatus 24 includes a neck portion surface temperature measuring apparatus 24a, which measures the surface temperature of the neck portion 2a of the bottle 2, a body portion surface temperature measuring apparatus 24b, which measures the surface temperature of the body portion 2b, and a bottom portion surface temperature measuring apparatus 24c, which measures the surface temperature of the bottom portion 2c, as shown in FIG. 5. The bottle surface temperature measuring apparatus 24 measures temperature by sensing infrared radiation emitted from the bottle 2, but not necessarily. Out of the surface temperatures of the neck portion 2a, the body portion 2b, and the bottom portion 2c of the molded bottle 2, the surface temperature of at least the body portion is measured. The surface temperature of the bottom portion 2c of the bottle 2 is measured by the bottom surface temperature measuring apparatus 24c and, the surface temperature of the bottom portion 2c of the bottle 2 may instead be measured by a bottom portion surface temperature measuring apparatus 24d, which measures the temperature of the side surface of the bottom portion 2c, as shown in FIG. 5.

The preform 1 is heated by the heating apparatus 6 to a temperature ranging from 90° C. to 130° C. The temperature of 130° C. is the crystallization temperature of polyethylene terephthalate, and when heated to a temperature higher than or equal to 130° C. and cooled slowly, the polyethylene terephthalate may crystallize and bleached. Assuming that the preform 1 is made of polyethylene terephthalate, the preform 1 is heated to a temperature lower than or equal to 130° C. The heated preform 1 is blow-molded, and the surface temperature of the molded bottle 2 is preferably lower than or equal to 70° C., which is lower than or equal to the glass transition point of polyethylene terephthalate. The reason for this is that when the surface temperature of the molded bottle is higher than 70° C., the bottle 2 may undesirably shrink and change in shape as the bottle 2 cools via the glass transition point.

In order that the sterilizer blasted in the form of a gas or mist of the sterilizer or a mixture thereof to the surface of the bottle 2 has an adequate sterilization effect, the surface temperature of the bottle 2 is equal to or higher than 40° C. or preferably equal to or higher than 50° C. when the sterilizer is blasted. The surface temperature of the bottle 2 is equal to or higher than 40° C. or preferably equal to or higher than 50° C. immediately before the sterilizer is blasted to the bottle 2 having been blow-molded, took out from the mold 20, and measured in terms of surface temperature. Below 40° C., sufficient sterilization effect is not provided. The specified temperature range of the surface temperature of the blow-molded bottle 2 therefore ranges from 40° C. to 70° C., preferably from 50° C. to 70° C.

In order that the surface temperature of the bottle 2 to which the sterilizer is blasted ranges from 40° C. to 70° C., the surface temperature of the mold 20 is controlled to fall within a temperature range specified by the mold temperature adjusting apparatus 54.

The temperatures of the neck portion mold 20a, the body portion mold 20b and the bottom portion mold 20c each must be controlled to fall within a specified temperature range. When the heated preform 1 is blow-molded, and the surface temperature of the molded bottle 2 is not higher than or equal to 40° C., which is the specified temperature, the sterilization effect of the sterilizer blasted in the form of a gas or mist or a mixture thereof to the surface of the bottle 2 can be inadequate. By controlling the temperature of a mold temperature adjusting medium circulated through the neck portion mold 20a, the body portion mold 20b, and the bottom portion mold 20c to fall within a specified temperature range, the surface temperature of the bottle 2 can be controlled to fall with an appropriate temperature range.

Figure 7:
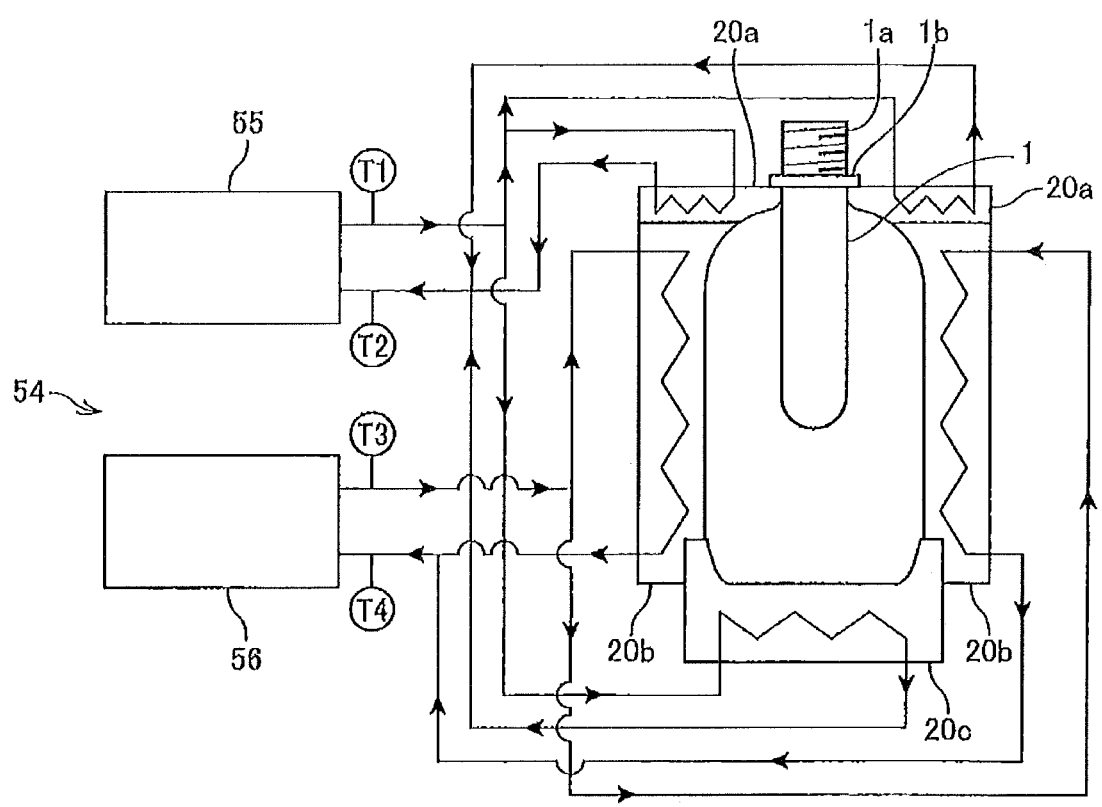
FIG. 7 shows a mold temperature adjusting apparatus provided in the aseptic filling machine according to the embodiment of the present invention.

As shown in FIG. 7, the aseptic filling machine is provided with the mold temperature adjusting apparatus 54 to adjust the temperature of the mold 20. The mold temperature adjusting apparatus 54 includes a mold temperature adjusting medium cooling tank 55, a mold temperature adjusting medium heating tank 56, a conduit for introducing the mold temperature adjusting medium from the mold temperature adjusting medium cooling tank 55 to the neck portion mold 20a and the bottom portion mold 20c, a conduit through which the mold temperature adjusting medium flows from the mold temperature adjusting medium heating tank 56 to the body portion mold 20b, a pump for causing the mold temperature adjusting medium to flow through the conduits, a valve and a temperature sensor. By circulating the mold temperature adjusting medium through the mold 20, the mold temperature adjusting apparatus 54 controls the temperatures of the neck portion mold 20a, the body portion mold 20b, and the bottom portion mold 20c. The mold temperature adjusting medium is a liquid, such as water or oil. The mold temperature adjusting medium does not become 0° C. or lower or is not heated to high temperatures, so that the mold temperature adjusting medium is preferably water.

The mold temperature adjusting apparatus 54 includes a mold temperature adjusting medium controlling apparatus that controls the temperature of the mold temperature adjusting medium, which controls the temperature of the mold. The mold temperature adjusting medium controlling apparatus cools the mold temperature adjusting medium in the mold temperature adjusting medium cooling tank 55 based on information from the temperature sensor. The neck portion 2a and the bottom portion 2c of the bottle 2 each have a large thickness and therefore have a large heat capacity, so that the surface temperature after molding does not become lower than or equal to 70° C. without cooling. An appropriate temperature range of the mold temperature adjusting medium in the mold temperature adjusting medium cooling tank 55 ranges from 5° C. to 20° C. A cooling apparatus for cooling the mold temperature adjusting medium is provided in the mold temperature adjusting medium cooling tank 55.

The mold temperature adjusting medium in the mold temperature adjusting medium heating tank 56 is preferably kept in the specified range of the temperature of the molded bottle 2 from 40° C. to 70° C. However, even when the temperature of the mold temperature adjusting medium in the mold temperature adjusting medium heating tank 56 exceeds 70° C., the surface temperature of the body portion 2b of the bottle 2 does not necessarily exceed 70° C., so that the temperature of the mold temperature adjusting medium in the mold temperature adjusting medium heating tank 56 may exceed 70° C. A heating apparatus, such as a heater, for heating the mold temperature adjusting medium and a cooling apparatus for cooling the mold temperature adjusting medium having been heated are provided in the mold temperature adjusting medium heating tank 56, and the temperature of the mold temperature adjusting medium is controlled by the mold temperature adjusting medium controlling apparatus.

The mold temperature adjusting apparatus 54 is provided with the mold temperature adjusting medium controlling apparatus. The mold temperature adjusting medium controlling apparatus controls the temperature of the mold temperature adjusting medium based on measured temperature data from the bottle surface temperature measuring apparatus 24 and the temperature sensor, which measures the temperature of the mold temperature adjusting medium.

As shown in FIG. 5, the temperature adjusting medium cooled in the mold temperature adjusting medium cooling tank 55 flows out of the mold temperature adjusting medium cooling tank 55 and is branched. One branch flow flows into two neck portion molds 20a, flows through a flow path in the neck portion molds 20a, flows out of the neck portion molds 20a and returns to the mold temperature adjusting medium cooling tank 55. The other branch flow flows into the bottom portion mold 20c, flows through a flow path in the bottom portion mold 20c, flows out of the bottom portion mold 20c and returns to the mold temperature adjusting medium cooling tank 55. The mold temperature adjusting medium need not be branched, and may flow from the mold temperature adjusting medium cooling tank 55 into the bottom portion mold 20c and then into the neck portion mold 20a.

The mouth portion 1a of the preform 1 is not heated to a temperature higher than or equal to 70° C. in the heating apparatus 6. The neck portion mold 20a is a mold for molding a shoulder portion of the bottle 2 from a part below the support ring 1b of the preform 1, as shown in FIG. 2(C). The part that forms the shoulder portion of the bottle 2 from the part below the support ring 1b of the preform 1 is formed of a relatively large amount of resin to be formed and has a relatively high heat capacity, so that the temperature of the part of the bottle 2 in contact with the neck portion mold 20a is less likely to decrease while the bottle 2 travels until the sterilizer is blasted thereto. The part of the preform 1 below the support ring 1b is heated to 90° C. to 130° C. by the heating apparatus 6. The temperature of the shoulder portion of the bottle 2 formed from the part of the preform 1 below the support ring 1b heated to 90° C. to 130° C. is around 70° C. or can be higher than 70° C., and the neck portion mold 20a needs to be cooled. To this end, in the mold temperature adjusting medium cooling tank 55, the mold temperature adjusting medium is kept in a temperature range from 5° C. to 20° C. Since the temperature of the mold temperature adjusting medium circulated through the neck portion mold 20a is kept in the temperature range from 5° C. to 20° C., the surface temperature of the part of the bottle 2 from the part below the support ring 1b to the shoulder portion thereof is higher than or equal to 40° C. when the sterilizer is blasted to the bottle 2. If the temperature of the mold temperature adjusting medium in the mold temperature adjusting medium cooling tank 55 is lower than 5° C., the surface temperature of the part of the bottle 2 from the part below the support ring 1b to the shoulder portion may be lower than 40° C. when the sterilizer is blasted to the bottle 2. If the temperature of the mold temperature adjusting medium is higher than 20° C., the surface temperature of the part of the bottle 2 from the part below the support ring 1b to the shoulder portion may be higher than 70° C. when the sterilizer is blasted. If the bottle 2 is slowly cooled from a temperature higher than 70° C., the molded bottle 2 may be deformed.

A part of the preform 1 that is molded to form the bottom portion 2c of the bottle 2 is heated to 90° C. to 130° C. by the heating apparatus 6. The bottom portion 2c of the bottle 2 is formed by pressing and stretching the bottom portion of the preform 1 with an extension rod. Therefore, the bottom portion of the bottle 2 is thinner than the bottom portion of the preform 1. However, the bottom portion of the bottle 2 is thicker and has a higher heat capacity than the body portion 2b of the bottle 2, and is not rapidly cooled by blow molding. When the bottom portion is slowly cooled, the resin forming the bottle 2 may crystalize, and the bottom portion may become brittle, so that the bottom portion mold 20c for molding the bottom portion 2c of the bottle 2 is cooled in the blow molding. To this end, the mold temperature adjusting medium in the mold temperature adjusting medium cooling tank 55 is kept at a temperature ranging from 5° C. to 20° C. Since the mold temperature adjusting medium circulated through the bottom portion mold 20c is kept at a temperature ranging from 5° C. to 20° C., the surface temperature of the bottom portion 2c of the bottle 2 is higher than or equal to 40° C. when the sterilizer is blasted to the bottle 2. If the temperature of the mold temperature adjusting medium in the mold temperature adjusting medium cooling tank 55 is lower than 5° C., the surface temperature of the bottom portion 2c of the bottle 2 may be lower than 40° C. when the sterilizer is blasted to the bottle 2. If the temperature of the mold temperature adjusting medium is higher than 20° C., the bottom portion 2c of the bottle 2 may crystallize, the bottom portion 2c of the bottle 2 may become brittle, and the bottle 2 may be damaged due to impact when dropped. In addition, the bottom portion 2c of the bottle 2 may also be deformed.

As shown in FIG. 7, the mold temperature adjusting medium heated in the mold temperature adjusting medium heating tank 56 flows into the upper portions of the two split parts of the body portion mold 20b, flows out of lower portions of the two parts of the body portion mold 20b, and then returns to the mold temperature adjusting medium heating tank 56. In the aseptic filling machine, immediately after the molding of the preform 1 into the bottle 2 is started, the mold temperature adjusting medium is heated in the mold temperature adjusting medium heating tank 56 and kept at a temperature ranging from 40° C. to 70° C.

Figure 8:
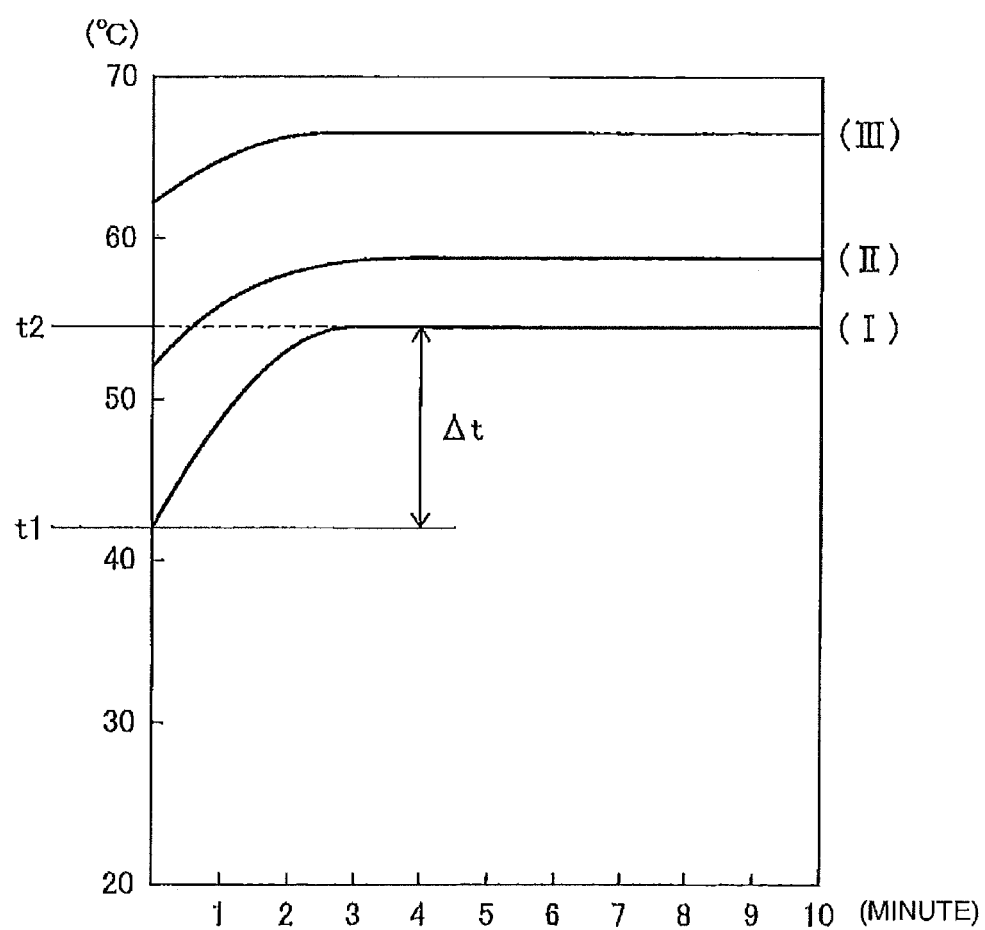
FIG. 8 shows the time elapsing after the blow molding is started versus the surface temperature of the blow-molded bottle in the aseptic filling method of related art.

However, even when the temperature of the mold temperature adjusting medium heated in the mold temperature adjusting medium heating tank 56 is fixed, the surface temperature of the body portion 2b of the molded bottle 2 immediately after the blow molding is started differs from the surface temperature after the number of times of the blow molding increases. For example, as shown in FIG. 8, when the temperature of the mold temperature adjusting medium is set at 45° C., the surface temperature of the body portion 2b of the molded bottle 2 immediately after the blow molding is started may become 43° C. because the bottle 2 took out from the mold 20 is cooled before reaching the bottle surface temperature measuring apparatus 24. At this point, the surface temperature of the body portion 2b is 43° C. (t1° C.). When the blow molding is started and the number of times of the blow molding increases over time, however, circulating the mold temperature adjusting medium directly to the body portion mold 20b conducts the heat from the heated preform 1 to the surface of the body portion mold 20b, so that the surface temperature of the body portion mold 20b rises to beyond 43° C. The surface temperature of the body portion 2b of the bottle 2 gradually rises, and the surface temperature of the body portion 2b of the bottle 2 took out from the mold 20 and measured by the bottle surface temperature measuring apparatus may become 54° C. (t2° C.). Since the mold temperature adjusting medium is heated by the mold at this point, the mold temperature adjusting medium in the body portion mold 20b is cooled to maintain the temperature of the body portion mold 20b at a temperature lower than or equal to the 54° C., to which the body portion mold 20b has been heated. The neck portion 2a and the bottom portion 2c of the bottle 2 also have low surface temperatures immediately after the blow molding is started, but the surface temperatures gradually rise over time. FIG. 8(I) shows the surface temperature of the body portion 2b of the bottle 2 over time immediately after the blow molding is started. FIG. 8(II) shows the surface temperature of the neck portion 2a of the bottle 2 over time immediately after the blow molding is started. FIG. 8(III) shows the surface temperature of the bottom portion 2c of the bottle 2 over time immediately after the blow molding is started.

Figure 9:
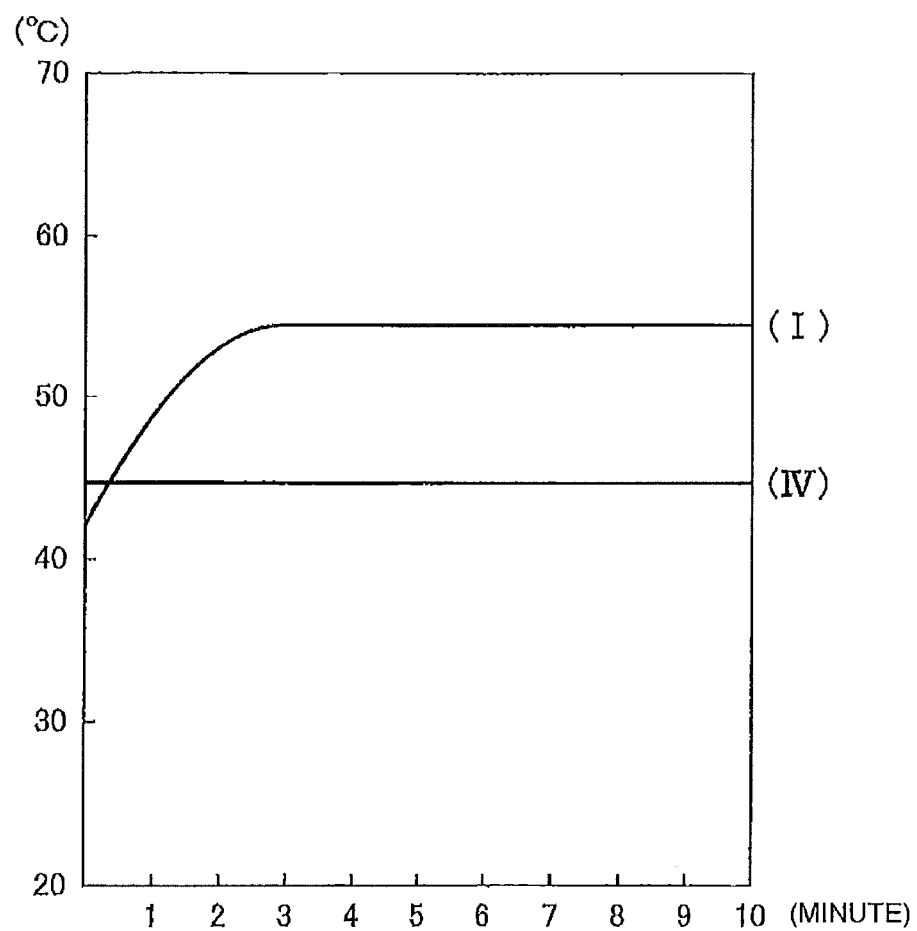
FIG. 9 shows the time elapsing after the blow molding is started versus the temperature of a mold temperature adjusting medium in a body portion of a mold and the surface temperature of a body portion of the blow-molded bottle in the aseptic filling method of related art.

The temperature (IV) of the mold temperature adjusting medium circulated through the body portion mold 20b is maintained at 45° C., but the surface temperature of the body portion 2b of the bottle 2 changes immediately after the blow molding starts and afterwards, as shown in (I), as described above with reference to FIG. 9. This changing surface temperature of the bottle 2 must remain constant over time immediately after the blow molding is started.

As the number of times of the blow molding increases, the temperature of the mold temperature adjusting medium flowing out of the body portion mold 20b increases. The preform 1 heated to a temperature ranging from 90° C. to 130° C. is stretched by high-pressure air, and the stretched resin at a temperature of 70° C. or higher is pressed against the body portion mold 20b. As a result, the temperature of the mold temperature adjusting medium tends to rise. To avoid this, the mold temperature adjusting medium heated in the mold temperature adjusting medium heating tank 56 is cooled and kept at a temperature ranging from 40° C. to 70° C.

Figure 10:
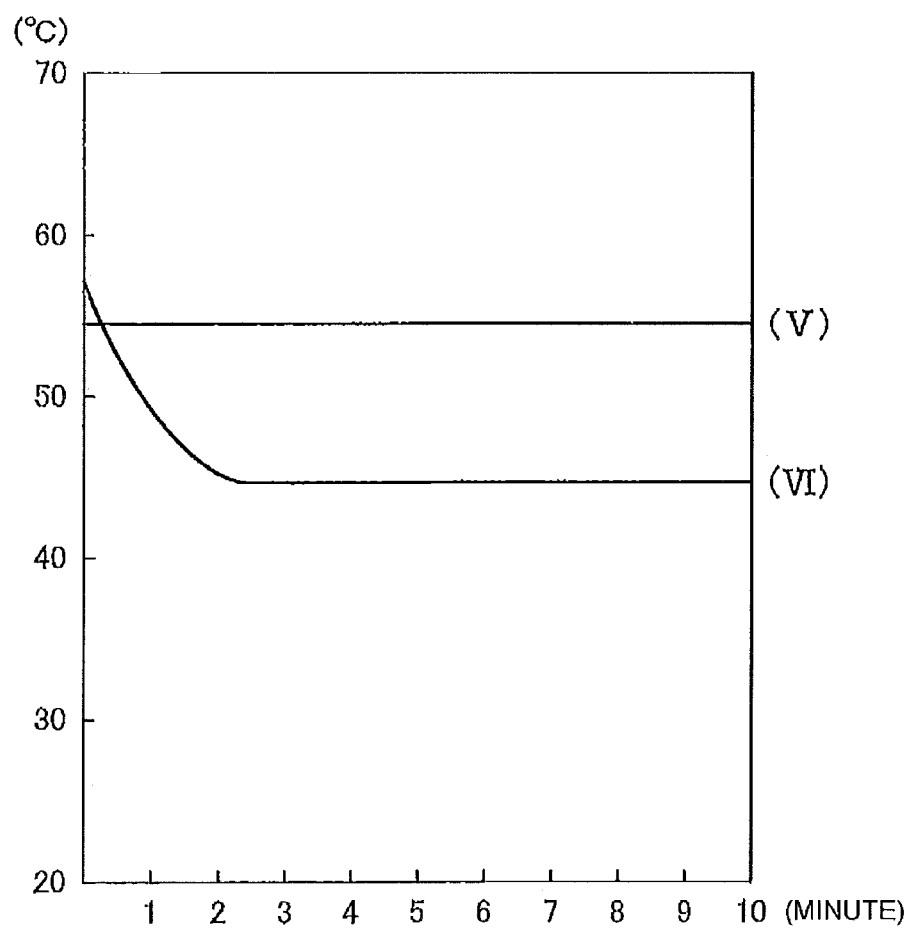
FIG. 10 shows the time elapsing after the blow molding is started versus the temperature of the mold temperature adjusting medium in the body portion of the mold and the surface temperature of the body portion of the blow-molded bottle according to the present invention.

Specifically, the temperature of the mold temperature adjusting medium is adjusted to adjust the temperature of the mold, so that the surface temperature of the bottle 2 has a fixed temperature over time immediately after the blow molding is started, as shown in FIG. 10. Provided that the temperature of the mold temperature adjusting medium circulated through the body portion mold 20b is maintained at 45° C., so that the surface temperature of the body portion 2b of the bottle 2 after a certain period has elapsed since the blow molding was started becomes 54° C., the temperature of the mold temperature adjusting medium circulated through the body portion mold 20b at the start of the blow molding must be set at a temperature higher than 45° C., which is the temperature after the certain period. This temperature must be higher than 54° C. Since the mold temperature adjusting medium is cooled until it flows out of the mold temperature adjusting medium heating tank 56 and circulates through the body portion mold 20b, the effect of the cooling must be taken into account. Assuming that by the mold temperature adjusting medium is cooled by 2° C., this temperature is set at 56° C. The temperature of the body portion 2b of the bottle 2 can be maintained at 54° C. over time immediately after the blow molding is started, as shown in FIG. 10(V), by setting the temperature of the mold temperature adjusting medium circulated through the body portion mold 20b at the start of the blow molding at 56° C. and adjusting the temperature after a certain period elapses from the start of the blow molding to gradually cool the mold temperature adjusting medium to 45° C., as shown in FIG. 10(VI).

The aforementioned values of the temperature of the mold temperature adjusting medium and the surface temperature of the body portion 2b of the molded bottle 2 are presented by way of example, and the measured surface temperature of the bottle 2 varies in accordance with the temperature to which the preform 1 is heated, the thickness of the body portion of the preform 1, the distance from the molded bottle 2 to the bottle surface temperature measuring apparatus 24, the ambient temperature, and other factors.

When the measured surface temperature of the bottle 2 does not fall within the specified temperature range, the mold temperature is adjusted to cause the surface temperature of the bottle 2 to fall within the specified temperature range. A bottle 2 having a temperature that does not fall within the specified temperature range is removed by the bottle removing apparatus 17 out of the aseptic filling machine. The mold temperature is adjusted by controlling the temperature of the mold temperature adjusting medium. When the measured surface temperature of the body portion 2b of bottle 2 is 43° C., the bottle 2 is not removed, provided that the specified temperature range is the range from 40° C. to 70° C. The reason for this is that the bottle 2 is adequately sterilized when a gas or mist of a sterilizer or a mixture thereof is blasted onto the bottle 2.

However, the amount of sterilizer blasted to sterilize a molded bottle 2 immediately after the start of the blow molding differs from the amount of sterilizer blasted to sterilize a molded bottle 2 after the blow molding is started and the number of times of the blow molding increases over time. As described above, the amount of sterilizer blasted to sterilize a bottle 2 with the body portion 2b having the temperature of 43° C. differs from the amount of sterilizer blasted to a bottle 2 with the body portion 2b having the temperature of 54° C. When a bottle 2 has a high surface temperature, the sterilizer is highly active, and the blasted amount of sterilizer is smaller than the amount blasted when the bottle 2 has a low surface temperature. To adequately sterilize all molded bottles 2, the amount of sterilizer necessary for sterilization of a molded bottle 2 immediately after the start of the blow molding must be blasted onto the bottles 2. As a result, an excessive amount of sterilizer is blasted onto a bottle 2 molded after the blow molding is started and the number of times of the blow molding increases over time.

To reduce the excessive amount of sterilizer, it is necessary to control the blasted amount of sterilizer, but it is cumbersome to control the blasted amount of sterilizer in accordance with the surface temperature of bottle 2 under measurement. In view of this, it is assumed that the surface temperature of the bottle 2 immediately after the blow molding is started is approximately to the surface temperature of the bottle 2 molded after the blow molding is started and the number of times of the blow molding increases over time. The blasted amount of sterilizer can thus be reduced.

To make the surface temperature of the bottle 2 immediately after the blow molding is started equal to the surface temperature of the bottle 2 molded after the blow molding is started and the number of times of the blow molding increases over time, it is necessary to set the temperature of the mold temperature adjusting medium at the start of the blow molding to a high temperature that is higher than the temperature of the mold temperature adjusting medium after the blow molding is started and a certain period elapses, and control the temperature of the mold temperature adjusting medium circulated through the mold 20 in such a way that the surface temperature of the bottle 2 measured immediately after the blow molding is started is approximately to the surface temperature of the bottle 2 measured after the certain period. That is, the mold temperature is so adjusted that the surface temperature of the molded bottle 2 falls within a narrow, constant temperature range. In the above description, the temperature of the mold temperature adjusting medium at the start of the blow molding is set to a high temperature that is higher than the temperature of the mold temperature adjusting medium after the blow molding is started and the certain period elapses. Instead, the high temperature to be set may be changed in accordance with the temperature to which the preform 1 is heated, the thickness of the body portion of the preform 1, the distance from the molded bottle 2 to the surface temperature measuring apparatus 24, the ambient temperature, and other factors, as described above, and may be higher by a range from 5° C. to 20° C.

The temperature of the mold temperature adjusting medium at the start of the blow molding is set to a high temperature that is higher than the temperature of the mold temperature adjusting medium after the blow molding is started and a certain period elapses, and the temperature to be set may be determined by the following method.

Let $t1°$ C. be the surface temperature of the body portion 2b of the bottle 2 at the start of the blow molding, and $t2°$ C. be the surface temperature of the body portion 2b of the bottle 2 after the blow molding is started and a specified period elapses. To bring the temperature $t1$ closer to the temperature $t2$, the temperature of the mold temperature adjusting medium circulated through the body portion mold 20b in the mold temperature adjusting apparatus 54 is raised by $\Delta t°$ C., which is the difference between $t2$ and $t1$, followed by the blow molding of the bottle 2. The specified period ranges from 1 to 5 minutes. Let $(t1+\Delta t)°$ C. be the temperature of the mold temperature adjusting medium, and $t3°$ C. be the surface temperature of the body portion 2b of the bottle 2 at the start of the blow molding, and the difference $\Delta t'°$ C. between $t2$ and $t3$ is fed back to the mold temperature adjusting apparatus 54, and the temperature of the mold temperature adjusting medium circulated through the body portion mold 20b in the mold temperature adjusting apparatus 54 is raised by $\Delta t'°$ C., which is the difference between $t2$ and $t3$, followed by the blow molding of the bottle 2. The operation described above is repeated to determine $(\Delta t+\Delta t' \ldots )°$ C. that allows $t1$ and $t2$ to be equal to each other. The temperature of the mold temperature adjusting medium at the start of the blow molding is higher by $(\Delta t+\Delta t' \ldots )°$ C. than the temperature of the mold temperature adjusting medium after the blow molding is started and the certain period elapses.

The mold temperature adjusting medium controlling apparatus includes a computation apparatus that determines $(\Delta t+\Delta t' \ldots )°$ C.

The temperature of the mold temperature adjusting medium is $(t1+(\Delta t° C.+\Delta t' \ldots ))°$ C. at the start of the blow molding, and when the blow molding starts, the heat of the heated preform 1 is conducted to the body portion mold 20b to raise the surface temperature of the mold. The temperature of the mold temperature adjusting medium therefore gradually lowers after the molding is started and a certain period elapses, and the temperature of the mold temperature adjusting medium is controlled by the mold temperature adjusting medium controlling apparatus to be $t1°$ C. after the specified period.

The temperature of the mold temperature adjusting medium at the start of the blow molding is set to a high temperature that is higher than the temperature of the mold temperature adjusting medium after the blow molding is started and a certain period elapses, as described above, and the temperature of the mold temperature adjusting medium is so lowered that the surface temperature of the bottle 2 does not exceed 70° C. The temperature of the mold temperature medium is so controlled that the surface temperature of the bottle 2 does not exceed 70° C. The controlled temperature range may range from 40° C. to 70° C., and the temperature of the mold temperature adjusting medium may exceed 70° C. as long as the surface temperature of the bottle 2 does not exceed 70° C.

The neck portion mold 20a and the bottom portion mold 20c have an inlet and an outlet for the mold temperature adjusting medium flowing therethrough at substantially the same level, so that the mold temperature adjusting medium can flow into the neck portion mold 20a and the bottom portion mold 20c at any part thereof. As for the body portion mold 20b, although the mold temperature adjusting medium flows into the body portion mold 20b at an upper part thereof and flows out of the body portion mold 20b at a lower part thereof in FIG. 5, the mold temperature adjusting medium may flows into the body portion mold 20b at a lower part thereof and flow out of the body portion mold 20b at an upper part thereof. The aseptic filling machine is provided with a plurality of the molds 20, and the mold temperature adjusting medium is caused to flow into all the molds 20 to control the temperature of the molds 20. Typically, a molding wheel 8 of the aseptic filling machine is provided with four to thirty-six molds 20.

A temperature sensor is provided in the mold temperature adjusting medium cooling tank 55 and the mold temperature adjusting medium heating tank 56, and based on the temperature information from the temperature sensor, the temperature of the mold temperature adjusting medium in the mold temperature adjusting medium cooling tank 55 and the mold temperature adjusting medium heating tank 56 is kept in a range specified by the mold temperature adjusting medium controlling apparatus. The mold temperature adjusting apparatus 54 is provided with another separate temperature sensor in the flow path of the mold temperature adjusting medium. By providing the temperature sensor in the flow path of the mold temperature adjusting medium, the temperature of the mold temperature adjusting medium flowing into and flowing out of the mold 20 can be kept track of.

A temperature sensor T1 is provided at a location where the mold temperature adjusting medium flows out of the mold temperature adjusting medium cooling tank 55, and a temperature sensor T2 is provided at a location where the mold temperature adjusting medium flows into the mold temperature adjusting medium cooling tank 55. A temperature sensor T3 is provided at a location where the mold temperature adjusting medium flows out of the mold temperature adjusting medium heating tank 56, and a temperature sensor T4 is provided at a location where the mold temperature adjusting medium flows into the mold temperature adjusting medium heating tank 56.

The temperature of the mold temperature adjusting medium is controlled by temperatures measured by the temperature sensors provided in the mold temperature adjusting medium cooling tank 55 and the mold temperature adjusting medium heating tank 56 and may instead be controlled by the temperature sensors T1 and T3 or T2 and T4 provided in the flow paths in the mold temperature adjusting medium cooling tank 55 and the mold temperature adjusting medium heating tank 56. The mold temperature adjusting medium flowing out of the mold temperature adjusting medium cooling tank 55 and the mold temperature adjusting medium heating tank 56 is cooled when releasing the heat into the flow paths or heated by the mold so that the temperature of the medium rises. The temperature sensor T4, when cooled or heated, may indicate a temperature lower by 0.1° C. to 2.0° C. than the temperature indicated by the temperature sensor T3. The temperature of the mold temperature adjusting medium may therefore be controlled by the temperature sensors T2 and T4.

When the temperature indicated by the temperature sensor T1 or T2 is outside the range from 5° C. to 20° C., or when the temperature indicated by the temperature sensor T3 or T4 is outside the range from 40° C. to 70° C., or when both the temperature indicated by the temperature sensor T1 or T2 and the temperature indicated by the temperature sensor T3 or T4 are outside the respective ranges, there is a possibility that the surface temperature of the bottle 2 to which the sterilizer is blasted is not higher than or equal to 40° C. or a possibility that the bottle 2 is deformed.

The bottle 2 passed to the inspection wheel 23 is subjected to measurement of the surface temperature by the bottle surface temperature measuring apparatus 24. The bottle 2 is further subjected to appearance inspection by a bottle appearance inspecting apparatus. The bottle inspecting apparatus is provided around the inspection wheel 23 and inspects the body portion 2b of the molded bottle 2, the support ring 1b, the top face of the mouth portion 1a of the molded bottle 2, the bottom portion 2c of the molded bottle 2, and the like. If it is determined that the bottle 2 has an abnormality, the bottle removing apparatus 17 removes the bottle 2 out of the aseptic filling machine.

The body portion 2b of the bottle 2, the support ring 1b, the mouth portion 1a of the bottle 2, the top face of the bottle 2, and the bottom portion 2c of the bottle 2 are imaged by a camera to inspect the condition of these portions. The taken image is processed by an image processing apparatus to determine whether there is any abnormality, such as a scratch, foreign matter, deformation, or discoloration. Any bottle 2 for which any of these is outside the allowable range is determined to be abnormal.

Any bottle 2 inspected by the bottle inspecting apparatus and not determined to be abnormal is conveyed to the bottle sterilizing apparatus 30 via wheels 25 and 26 in the atmosphere separation chamber 27, which is provided between the blow-molding apparatus 16 and the bottle sterilizing apparatus 30, to prevent the gas or mist of the sterilizer or the mixture thereof used in the bottle sterilizing apparatus 30 from flowing into the blow-molding apparatus 16.

The wheel 25 is provided with the bottle removing apparatus 17, which removes any bottle 2 having been molded with the measured surface temperature of the bottle 2 being outside the specified temperature range. Further, any bottle 2 determined to be abnormal by the bottle appearance inspection apparatus is also removed.

The bottle 2 conveyed to the bottle sterilizing apparatus 30 is sterilized on the wheel 28. The sterilization is achieved by bringing the gas or mist of the sterilizer or the mixture thereof into contact with the bottle 2. The step of blasting the sterilizer to the bottle 2 to sterilize the bottle 2 is shown in FIG. 3(E-1). To blast the gas of the sterilizer to the bottle 2, a sterilizer gas blasting nozzle 31 is provided. The sterilizer gas blasting nozzle 31 is fixed in such a manner that a nozzle hole at the tip end thereof can be directly opposed to the opening of the mouth portion 1a of the bottle 2 traveling directly below the sterilizer gas blasting nozzle 31. As required, a sterilizer gas blasting tunnel 32 is provided below the sterilizer gas blasting nozzle 31 along the travel path of the bottle 2 as shown in FIG. 3(E-1). One or more sterilizer gas blasting nozzles 31 can be provided. The gas of the sterilizer blasted to the bottle 2 flows into the bottle 2 and sterilizes the inner surface of the bottle 2. At the same time, the bottle 2 travels in the sterilizer gas blasting tunnel 32, and the gas or mist of the sterilizer or the mixture thereof also flows onto the outer surface of the bottle 2 and sterilizes the outer surface of the bottle 2.

As shown in FIG. 3(E-2), the sterilizer gas blasting nozzle 31 may be caused to follow the conveyed bottle 2 and the sterilizer gas blasting nozzle 31 may be inserted into the bottle 2 to directly blast the gas or mist of the sterilizer or the mixture thereof to the inner surface of the bottle 2. Any of the gas or mist of the sterilizer or the mixture thereof overflowing from the bottle 2 collides against a guide member 31a provided to surround the sterilizer gas blasting nozzle 31, flows onto the outer surface of the bottle 2, and comes into contact with the outer surface of the bottle 2. The guide member 31a is provided with a flange portion that is coaxial with the sterilizer gas blasting nozzle 31 and an annular wall portion that protrudes from the flange portion along the circumference thereof.

Figure 4:
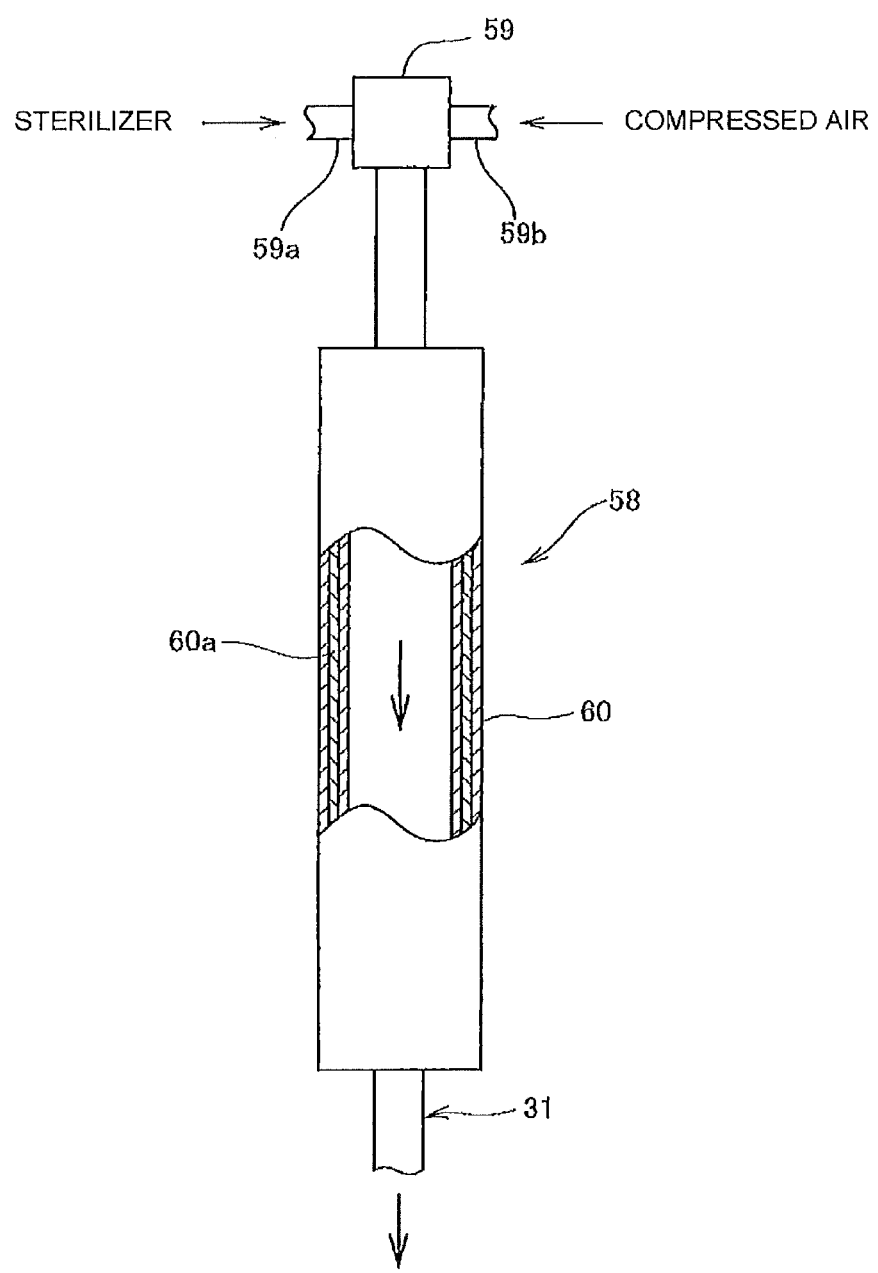
FIG. 4 shows a sterilizer gas generator incorporated in the aseptic filling machine according to the embodiment of the present invention.

The gas or mist of the sterilizer or the mixture thereof is the sterilizer gasified by a sterilizer gas generator 58 shown in FIG. 4, or a mist formed by condensation of the gasified sterilizer, or a mixture thereof. The sterilizer gas generator 58 includes a sterilizer supply portion 59, which is a twin-fluid spray nozzle that supplies the sterilizer in the form of drops, and a vaporizing portion 60, which vaporizes the sterilizer supplied from the sterilizer supply portion 59 by heating the sterilizer to a temperature lower than or equal to the decomposition temperature thereof. The sterilizer supply portion 59 is configured to guide the sterilizer and compressed air that are introduced via a sterilizer supply path 59a and a compressed air supply path 59b, respectively, and to spray the sterilizer into the vaporizing portion 60. The vaporizing portion 60 is a pipe that incorporates a heater 60a disposed between inner and outer walls thereof, and heats and vaporizes the sterilizer blasted into the pipe. The gas of the vaporized sterilizer is ejected out of the vaporizing portion 60 via the sterilizer gas blasting nozzle 31. The vaporizing portion 60 may be heated by induction heating instead of the heater 60a.

As the operating condition of the sterilizer supply portion 59, for example, the pressure of the compressed air is adjusted to fall within the range from 0.05 MPa to 0.6 MPa. The sterilizer may be supplied by gravity or pressure, and the amount of the supplied sterilizer can be arbitrarily set. For example, the sterilizer is supplied to the sterilizer supply path 59a by an amount ranging from 1 g/min. to 100 g/min. Furthermore, the sprayed sterilizer is vaporized by heating the inner surface of the vaporizing portion 60 to a temperature ranging from 140° C. to 450° C.

As shown in FIG. 3(E), the gas of the sterilizer is blasted via the sterilizer gas blasting nozzle 31 to the bottle 2. Although the blasting amount of the gas or mist of the sterilizer or the mixture thereof is arbitrarily set, the blasting amount is determined by the amount of the sterilizer supplied to the sterilizer gas generator 58 and the duration of blasting. A plurality of sterilizer gas generators 58 may be provided. The blasting amount also depends on the size of the bottle 2.

The sterilizer preferably contains at least hydrogen peroxide. An appropriate content of hydrogen peroxide ranges from 0.5% by mass to 65% by mass. If the content is lower than 0.5% by mass, the sterilization power may be insufficient in some cases, while if the content is higher than 65% by mass, the sterilizer will be difficult to handle from the viewpoint of safety. A further preferable content ranges from 0.5% by mass to 40% by mass. When the content is lower than or equal to 40% by mass, it is easier to handle the sterilizer, and the residual amount of the sterilizer in the bottle 2 after sterilization can be reduced since the concentration of hydrogen peroxide is low.

When a hydrogen peroxide solution is used as the sterilizer, the blasting amount of the gas of the hydrogen peroxide solution is as follows. The amount of the hydrogen peroxide adhering to the inner surface of the bottle 2 that derives from the gas of the hydrogen peroxide solution blasted to the inner surface of the bottle 2 via the sterilizer gas blasting nozzle 31 preferably ranges from 30 μL/bottle to 150 μL/bottle, and more preferably, from 50 μL/bottle to 100 μL/bottle, when the hydrogen peroxide solution contains 35% by mass of hydrogen peroxide. The hydrogen peroxide concentration of the gas of the hydrogen peroxide solution blasted to the bottle 2 preferably ranges from 2 mg/L to 20 mg/L, and more preferably from 5 mg/L to 10 mg/L.

The sterilizer contains water. However, the sterilizer may contain one or more of alcohols such as methyl alcohol, ethyl alcohol, isopropyl alcohol, n-propyl alcohol, and butyl alcohol, ketones such as acetone, methyl ethyl ketone, and acetylacetone, and glycol ethers and the like.

The sterilizer may further contain an additive agent such as a compound having a sterilizing effect such as peracetic acid, acetic acid, or any other organic acid, sodium hypochlorite, or any other chlorine compound, or ozone; a cationic surfactant; a non-ionic surfactant; or a phosphate compound.

The bottle 2 sterilized in the bottle sterilizing apparatus 30 is conveyed to the air-rinsing apparatus 34 via a wheel 29, as shown in FIG. 1. On an air-rinsing wheel 35 shown in FIG. 1, the bottle 2 is in the upright position, and aseptic air is blasted to the bottle 2 via an air-rinsing nozzle 38 as shown in FIG. 3(F-1). Although the aseptic air can have room temperature, the aseptic air is preferably heated. The aseptic air has effects of discharging any sterilizer remaining in the bottle 2, decomposing the remaining sterilizer to increase the sterilization effect, and discharging foreign matter, if any, in the bottle 2. Alternatively, the aseptic air may be blasted to the bottle 2 in the inverted position as shown in FIG. 3(F-2). In the inverted position, foreign matter can be more effectively discharged than in the upright position. Further, if a guide member that surrounds the air-rinsing nozzle 38 is provided as with the sterilizer gas blasting nozzle 31 in FIG. 3(E-2), the aseptic air introduced into the bottle 2 and then overflowing via the mouth portion 1a collides against the guide member and also rinses the outer periphery of the mouth portion 1a, so that the temperature of the outer periphery of the mouth portion 1a rises, and the outer periphery of the mouth portion 1a is more effectively sterilized.

The air-rinsing nozzle 38 may be capable of vertical movement and may blast aseptic air into the bottle 2 while moving vertically. Instead of the aseptic air, aseptic water may be introduced into the bottle 2 to rinse the interior of the bottle 2. Further, both the aseptic air and the aseptic water may be used in combination to rinse the bottle 2.

The bottle 2 having been air-rinsed by the air-rinsing apparatus 34 is conveyed to the filling apparatus 39 via a wheel 37, as shown in FIG. 1. In the filling apparatus 39, on a filling wheel 40 shown in FIG. 1, the bottle 2 is filled with a content via a filling nozzle 42 in a filling step shown in FIG. 3(G). The content is sterilized in advance, and the bottle 2 is filled with a certain amount of content, such as a drink, via the filling nozzle 42 traveling in sync with the bottle 2.

The bottle 2 filled with the content is conveyed to the sealing apparatus 44 via a wheel 43 shown in FIG. 1. On a sealing wheel 45 provided in the sealing apparatus 44, in a sealing step shown in FIG. 3(H), the lid member 3, which is a sealing member sterilized by the lid member sterilizing apparatus 52, is supplied to the sealing wheel 45 through a sterilized lid member conveyance path 51 and via a lid supplying wheel 53a and a lid receiving wheel 53b, and is wrapped around and fastened to the mouth portion 1a of the bottle 2 by a capper that is not shown to seal the bottle 2.

The sealed bottle 2 is passed from the gripper 22 on the sealing wheel 45 to the gripper 22 on a discharging wheel 48 of the discharging apparatus 47. The bottle 2 having passed to the discharging wheel 48 is placed on the discharging conveyor 50. The bottle 2 placed on the discharging conveyor 50 is discharged out of the aseptic filling machine.

The interiors of the sterilizing portion chamber 33, the air-rinsing portion chamber 36, the filling portion chamber 41, the sealing portion chamber 46, and the discharging portion chamber 49 are sterilized before operation of the aseptic filling machine.

The sterilizer is blasted into each of the chambers that need to be sterilized in such a manner that the sterilizer adheres to the entire interior of the chamber. The blasted sterilizer sterilizes the interior of each of the chambers. The same sterilizer as that used for sterilizing the bottle 2 can be used, and a sterilizer containing peracetic acid or hydrogen peroxide is preferably used. Blasting the sterilizer may be replaced with blasting different sterilizers multiple times.

Second Embodiment

In the first embodiment, the surface temperatures of the neck portion 2a, the body portion 2b, and the bottom portion 2c of the molded bottle 2 are measured, and the mold temperatures of the neck portion mold 20a, the body portion mold 20b, and the bottom portion mold 20c of the mold 20 are so adjusted that the measured surface temperatures of the bottle 2 fall within the specified temperature range, whereas in a second embodiment, the surface temperature of at least the body portion mold 20b out of the surface temperatures of the neck portion mold 20a, the body portion mold 20b, and the bottom portion mold 20c of the mold 20 is measured, and the mold temperatures of the neck portion mold 20a, the body portion mold 20b, and the bottom portion mold 20c of the mold 20 are so adjusted that the temperature of the mold 20 falls within a specified temperature range. The only difference from the first embodiment is the point described above, and the step of blow-molding the preform 1 into the bottle 2 and the preceding steps, and the step of sterilizing the molded bottle 2 and the following steps are the same as those in the first embodiment.

Figure 6:
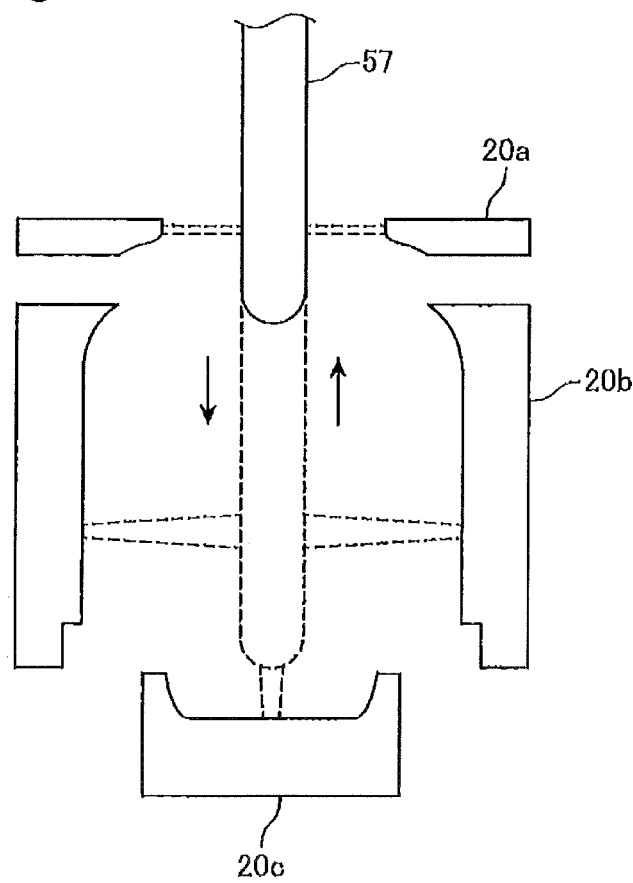
FIG. 6 shows a mold surface temperature measuring apparatus provided in the aseptic filling machine according to the embodiment of the present invention.

FIG. 6 shows a mold surface temperature measuring apparatus 57, which measures the surface temperature of the mold 20 with a non-contact thermometer. The mold surface temperature measuring apparatus 57 has at least three sensors including the sensor that measures the surface temperature of the bottom portion mold 20c and the two sensors that move vertically and measure the surface temperature of the neck portion mold 20a and the body portion mold 20b, which are split molds each formed by two parts. When separately measuring each part of the neck portion mold 20a and the body portion mold 20b, the mold surface temperature measuring apparatus 57 has five sensors.

The temperature sensor measures temperature by sensing the infrared radiation emitted from the mold 20. However, the present invention is not limited to this. Although it had been difficult to measure the temperature of a mirror-like metal surface, such as the surface of the mold 20, because of its low emissivity, sensors capable of measuring the temperature of such a surface have been recently developed. The tip end of the sensor is preferably directed substantially normal to the measured surface.

The surface temperature of the bottom portion mold 20c can be directly measured by the sensor provided at the tip end of the mold surface temperature measuring apparatus 57. When measuring the surface temperature of the neck portion mold 20a and the body portion mold 20b, the tip end of the sensor is not directed perpendicularly to the measured surface. However, a mirror that reflects the infrared radiation emitted from the measured surface at an angle of 90 degrees can be attached to the tip end of the sensor to enable measurement of the surface temperature of the neck portion mold 20a and the body portion mold 20b, which are located at the sides of the mold surface temperature measuring apparatus 57. Provided that the diameter of the sensor is 15 mm$\phi$, for example, the total width of two sensors incorporated in the mold surface temperature measuring apparatus 57 is about 30 mm, and the sensors can be inserted into the open mold 20. The sensor for the bottom portion mold 20c and the sensors for the neck portion mold 20a and the body portion mold 20b are incorporated in different parts of the mold surface temperature measuring apparatus 57, so that the mold surface temperature measuring apparatus 57 does not have to have a width greater than 30 mm.

After the mold 20 is opened after blow molding and the bottle 2 is took out, the mold surface temperature measuring apparatus 57 is inserted into the open mold via the side surface of the mold 20. As shown in FIG. 6, after the inserted, the mold surface temperature measuring apparatus 57 incorporating at least three sensors measured the surface temperatures of the neck portion mold 20a, the body portion mold 20b, and the bottom portion mold 20c while lowering the mold surface temperature measuring apparatus 57. Alternatively, the mold surface temperature measuring apparatus 57 incorporating five temperature sensors may be inserted into the mold 20 to measure the surface temperature of five parts of the mold 20 at the same time. The mold surface temperature measuring apparatus 57 need not be provided for all of the molds.

Instead of inserting the mold surface temperature measuring apparatus 57 into the mold 20 from above the mold 20, the mold surface temperature measuring apparatus 57 may be inserted into the open mold 20 from a side of the open mold 20 to measure the surface temperature of the mold 20.

Figure 11:
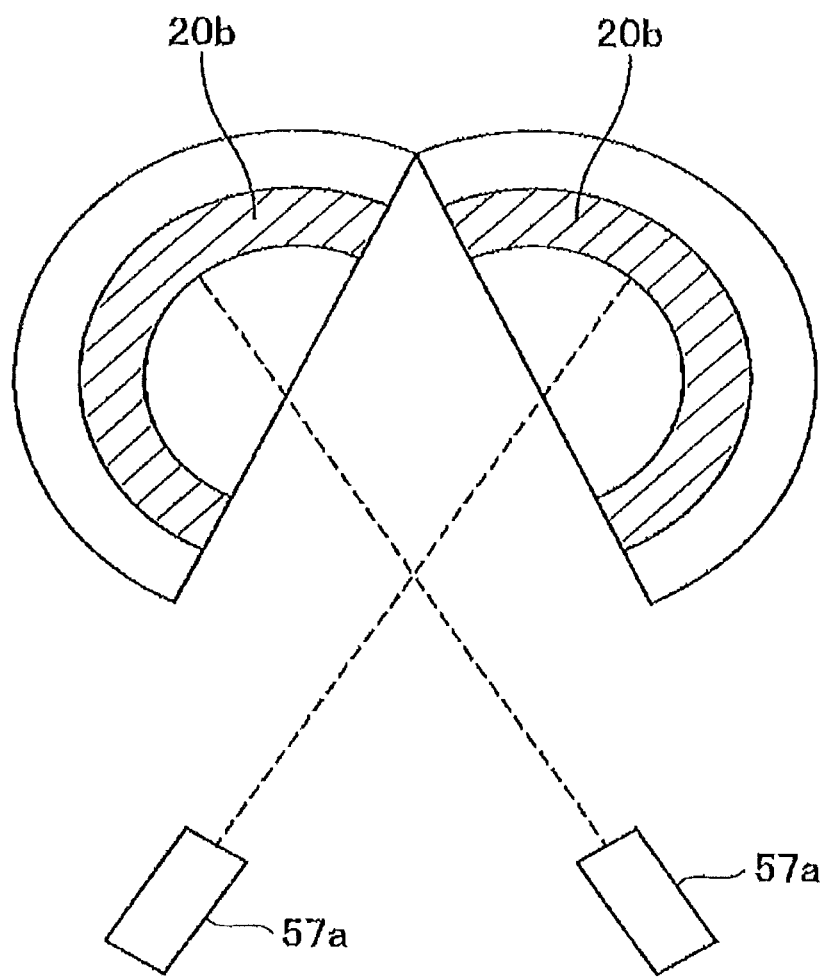
FIG. 11 shows a mold surface temperature measuring apparatus that is provided in the aseptic filling machine according to the embodiment of the present invention and externally measured the body portion mold.

The mold surface temperature measuring apparatus 57 does not have to be inserted into the mold 20 to measure the surface temperature of the mold 20. As shown in FIG. 11, after the mold 20 is opened after blow molding and the bottle 2 is took out, the surface temperature of the mold 20 may be measured from outside the mold 20 with a mold surface temperature measuring apparatus 57a. As shown in FIG. 11, at least two mold surface temperature measuring apparatuses 57a are provided to measure the surface temperature of the body portion mold 20b. Although FIG. 11 shows a mold for forming a round-shape bottle 2, the mold can be any mold for forming a bottle having a rectangular or polygonal shape.

Figure 12:
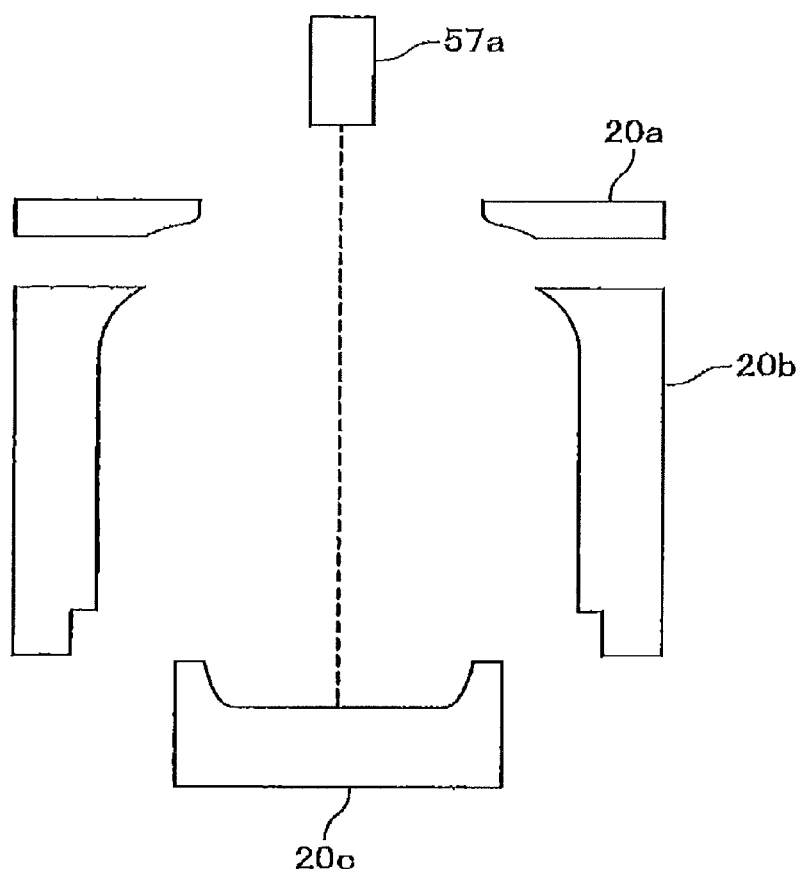
FIG. 12 shows a mold surface temperature measuring apparatus that is provided in the aseptic filling machine according to the embodiment of the present invention and externally measured a bottom portion mold.

As shown in FIG. 12, if the mold surface temperature measuring apparatus 57a that receives the infrared radiation traveling perpendicularly from the surface of the bottom portion mold 20c is provided above the mold 20, the surface temperature of the bottom portion mold 20c can be measured without inserting the mold surface temperature measuring apparatus 57 into the mold 20.

The measured temperature of the body portion mold 20b measured by the mold surface temperature measuring apparatus 57 must ranges from 40° C. to 70° C. The reason for this is that the body portion 2b of the bottle 2 is relatively thin and is therefore greatly affected by the surface temperature of the body portion mold 20b. If the surface temperature of the body portion mold 20b under measurement does not fall within the range from 40° C. to 70° C., the molded bottle 2 is removed by the bottle removing apparatus 17 out of the aseptic filling machine.

Even if the temperatures of the neck portion mold 20a and the bottom portion mold 20c do not fall within the range from 40° C. to 70° C., the surface temperatures of the neck portion 2a and the bottom portion 2c of the molded bottle 2 fall within the range from 40° C. to 70° C. The neck portions 2a and the bottom portion 2c are each formed of a relatively large amount of resin and has a relatively high heat capacity, so that the temperature of the parts of the bottle 2 in contact with the neck portion mold 20a and the bottom portion mold 20c are less likely to decrease while the bottle 2 travels until the sterilizer is blasted thereto. The lower portion of the support ring 1b and the bottom portion of the preform 1 are heated by the heating apparatus 6 to a temperature ranging from 90° C. to 130° C. The temperature of the shoulder portion and the bottom portion of the bottle 2 formed from the part of the preform 1 below the support ring 1b heated to 90° C. to 130° C. is around 70° C. or can be higher than 70° C., and the neck portion mold 20a and the bottom portion mold 20c need to be cooled to 40° C. or lower. The temperatures range from 5° C. to 20° C.

If the temperatures of the neck portion mold 20a, the body portion mold 20b, and the bottom portion mold 20c of the mold 20 fall within the specified temperature range, the molded bottle 2 is conveyed to the bottle sterilizing apparatus 30. If the temperatures of the five parts of the neck portion mold 20a, the body portion mold 20b, and the bottom portion mold 20c do not fall within the specified temperature range, there is a possibility that the surface temperature of the bottle 2 to which the sterilizer is blasted is not higher than or equal to 40° C., so that the bottle 2 is not adequately sterilized even if the sterilizer is blasted to the bottle 2.

To allow the surface temperature of the bottle 2 to which the sterilizer is blasted to fall within the specified temperature range from 40° C. to 70° C., the surface temperature of the mold 20 is controlled by the mold temperature adjusting apparatus 54 to fall within the specified temperature range.

The temperatures of the neck portion mold 20a, the body portion mold 20b, and the bottom portion mold 20c must be controlled to fall within the specified temperature range. When the heated preform 1 is blow-molded into the bottle 2, the surface temperature of the molded bottle 2 must be higher than or equal to the predetermined temperature of 40° C. This is because if the surface temperature is lower than the predetermined temperature of 40° C., the sterilization effect of the gas or mist of the sterilizer or the mixture thereof blasted to the surface of the bottle 2 can be inadequate.

If the measured surface temperature of the mold 20 does not fall within the specified temperature range, the mold temperature is adjusted by the mold temperature adjusting apparatus 54 to cause the surface temperature of the bottle 2 to fall within the specified temperature range. A bottle 2 having a temperature that does not fall within the specified temperature range is removed by the bottle removing apparatus 17 out of the aseptic filling machine. The mold temperature is adjusted by controlling the temperature of the mold temperature adjusting medium. By controlling the temperature of a mold temperature adjusting medium circulated through the neck portion mold 20a, the body portion mold 20b, and the bottom portion mold 20c to fall within the specified temperature range, the surface temperature of the mold 20 can be controlled to fall within the specified temperature range. The temperature of the mold temperature adjusting medium is controlled by a mold temperature adjusting medium temperature controlling apparatus.

As the number of times of the blow molding increases, the temperature of the mold temperature adjusting medium flowing out of the body portion mold 20b increases. The preform 1 heated to a temperature ranging from 90° C. to 130° C. is stretched by high-pressure air, and the stretched resin at a temperature of 70° C. or higher is pressed against the body portion mold 20b. As a result, the temperature of the mold temperature adjusting medium tends to rise. To avoid this, the mold temperature adjusting medium heated in the mold temperature adjusting medium heating tank 56 is cooled and kept at a temperature ranging from 40° C. to 70° C. by the mold temperature adjusting medium temperature controlling apparatus.

The amount of sterilizer blasted to sterilize the bottle 2 molded immediately after the blow molding is started differs from the amount of sterilizer blasted to sterilize bottle 2 molded after the blow molding is started and the number of times of the blow molding increases over time. When a bottle 2 has a high surface temperature, the sterilizer is highly active, and the blasted amount of sterilizer is smaller than the amount blasted when the bottle 2 has a low surface temperature. To adequately sterilize all molded bottles 2, the amount of sterilizer necessary for sterilization of a molded bottle 2 immediately after the start of the blow molding must be blasted onto the bottles 2. As a result, an excessive amount of sterilizer is blasted onto a bottle 2 molded after the blow molding is started and the number of times of the blow molding increases over time.

To reduce the amount of excess sterilizer, the surface temperature of the molded bottle 2 needs to be kept relatively high. For example, to allow the surface temperature of the molded bottle 2 to be 60° C., at least the surface temperature of the body portion 20b of the mold 20 needs to be controlled to a temperature higher than 60° C., for example, 62° C. at the start of the bottle molding in consideration of the fact that the mold temperature adjusting medium is cooled before flowing from the mold temperature adjusting medium heating tank 56 into the body portion mold 20b.

To make the surface temperature of the mold 20 immediately after the blow molding is started equal to the surface temperature of the mold 20 after the blow molding is started and the number of times of the blow molding increases over time, it is necessary to set the temperature of the mold temperature adjusting medium at the start of the blow molding to be higher than the temperature of the mold temperature adjusting medium after the blow molding is started and a certain period elapses, and control the temperature of the mold temperature adjusting medium circulated through the mold 20 based on the measured surface temperature of the mold 20 after the blow molding is started to lower the temperature of the mold temperature adjusting medium circulated through the mold. For example, when the temperature of the mold temperature adjusting medium flowing into the body portion mold 20b of the mold 20 at the start of the blow molding is set at 62° C., the surface temperature of the body portion mold 20b of the mold 20 gradually rises as the number of times of the blow molding increases. To maintain the surface temperature of the molded bottle 2 at 60° C., the surface temperature of the body portion mold 20b of the mold 20 needs to be cooled to a temperature lower than or equal to 60° C. For example, the temperature of the mold temperature adjusting medium flowing from the mold temperature adjusting medium heating tank 56 into the body portion mold 20b needs to be lower than or equal to 55° C. In this case, the temperature of the mold temperature adjusting medium at the start of the blow molding is set to be higher by at least 5° C. than the temperature of the mold temperature adjusting medium after the blow molding is started and a certain period elapses. The temperature of the mold temperature adjusting medium set at the start of the blow molding may be changed in accordance with the temperature to which the preform 1 is heated, the thickness of the body portion of the preform 1, the distance from the molded bottle 2 to the surface temperature measuring apparatus 24, the ambient temperature, and other factors and the high temperature may be higher by a range from 5° C. to 20° C.

The aforementioned control of the temperature of the mold temperature adjusting medium is performed by the mold temperature adjusting medium controlling apparatus provided in the mold temperature adjusting apparatus 54 based on measured temperature data from the mold surface temperature measuring apparatus 57 and the temperature sensors (T1, T2, T3, and T4), which measure the temperature of the mold temperature adjusting medium.

The temperature of the mold temperature adjusting medium at the start of the blow molding is set to a high temperature that is higher than the temperature of the mold temperature adjusting medium after the blow molding is started and a certain period elapses, and the temperature of the mold temperature adjusting medium is so lowered that the surface temperature of the molded bottle 2 does not exceed 70° C. The temperature of the mold temperature adjusting medium may instead be controlled not to exceed a temperature lower than or equal to 70° C.

Although the present invention is configured as described above, the present invention is not limited to the embodiments described above, and various modifications can be made without departing from the spirit of the present invention.

REFERENCE SIGNS LIST 1 preform
2 bottle
6 heating apparatus
16 blow-molding apparatus
17 bottle removing apparatus
20 mold
20a neck portion mold
20b body portion mold
20c bottom portion mold
24 bottle surface temperature measuring apparatus
30 bottle sterilizing apparatus
39 filling apparatus
44 sealing apparatus
49 discharging portion chamber
54 mold temperature adjusting apparatus
55 mold temperature adjusting medium cooling tank
56 mold temperature adjusting medium heating tank
57 mold surface temperature measuring apparatus

The invention claimed is:

1. An aseptic filling method comprising:
heating a preform and sealing the heated preform in a mold formed of a neck portion, a body portion, and a bottom portion;
blow-molding the preform sealed in the mold into a bottle;
measuring a surface temperature of at least the body portion out of surface temperatures of the neck portion, the body portion, and the bottom portion of the molded bottle;
controlling a temperature of a mold temperature adjusting medium circulated through the mold to control mold temperatures of the neck portion, the body portion, and the bottom portion of the mold in such a way that the measured surface temperature of the bottle falls within a specified temperature range;
causing a gas or mist of a sterilizer or a mixture thereof to come into contact with the molded bottle;
sterilizing a surface of the bottle;
filling the sterilized bottle with a sterilized content; and
sealing the bottle filled with the content with a sterilized lid member,
wherein when the blow molding is started, the temperature of the mold temperature adjusting medium is set to a high temperature that is higher than the temperature of the mold temperature adjusting medium after the blow molding is started and a certain period elapses, and the temperature of the mold temperature adjusting medium circulated through the mold is so controlled that the surface temperature of the bottle measured immediately after the blow molding is started is approximately to the surface temperature of the bottle measured after the certain period.

2. The aseptic filling method according to claim 1,
wherein let t1° C. be the surface temperature of the body portion of the bottle at the start of the blow molding, and
t2° C. be the surface temperature of the body portion of the bottle after the blow molding is started and a specified period elapses,
the temperature of the mold temperature adjusting medium circulated through the body portion mold is raised by Δt° C., which is a difference between t2 and t1, followed by the blow molding of the bottle,
when the surface temperature of the body portion of the bottle at the start of the blow molding is t3° C., the difference Δt'° C. between t2 and t3 is fed back to control the temperature of the mold temperature adjusting medium,
the temperature of the mold temperature adjusting medium circulated through the body portion mold is raised by Δt'° C., followed by the blow molding of the bottle, and
the above operation is repeated to determine (Δt+ Δt' ... )° C., which allows t1 and t2 to be equal to each other and which is defined as the high temperature.

3. An aseptic filling method comprising:
heating a preform;
sealing the heated preform in a mold formed of a neck portion, a body portion, and a bottom portion;
blow-molding the preform sealed in the mold into a bottle;
measuring a surface temperature of at least the body portion out of surface temperatures of the neck portion, the body portion, and the bottom portion of the mold;
controlling a temperature of a mold temperature adjusting medium circulated through the mold to control mold temperatures of the neck portion, the body portion, and the bottom portion of the mold in such a way that the measured surface temperature falls within a specified temperature range;

causing a gas or mist of a sterilizer or a mixture thereof to come into contact with the bottle molded by the mold having the adjusted mold temperatures;

sterilizing a surface of the bottle and filling the sterilized bottle with a sterilized content; and sealing the bottle filled with the content with a sterilized lid member, wherein when the blow molding is started, the temperature of the mold temperature adjusting medium is set to a high temperature that is higher than the temperature of the mold temperature adjusting medium after the blow molding is started and a certain period elapses, and the temperature of the mold temperature adjusting medium circulated through the mold is so controlled that the surface temperature of the mold measured immediately after the blow molding is started is approximately to the surface temperature of the mold measured after the certain period.

4. An aseptic filling machine comprising:

a heating apparatus that heats a preform;

a mold formed of a neck portion, a body portion, and a bottom portion that seal the preform to blow-mold the heated preform into a bottle;

a blow-molding apparatus that blow-molds the preform sealed in the mold into the bottle;

a bottle surface temperature measuring apparatus that measures a surface temperature of at least the body portion out of surface temperatures of the neck portion, the body portion, and the bottom portion of the blow-molded bottle;

a mold temperature adjusting apparatus that includes a mold temperature adjusting medium controlling apparatus that controls a temperature of a mold temperature adjusting medium circulated through the mold formed of the neck portion, the body portion, and the bottom portion and adjusts a temperature of the mold formed of the neck portion, the body portion, and the bottom portion;

a bottle sterilizing apparatus that blasts a gas or mist of a sterilizer or a mixture thereof to the bottle to sterilize the bottle;

a filling apparatus that fills the sterilized bottle with a sterilized content;

a sealing apparatus that seals the bottle filled with the content with a sterilized lid member; and a conveying apparatus that conveys the preform or the bottle from the heating apparatus to the sealing apparatus, wherein when the blow molding is started, the mold temperature adjusting medium controlling apparatus sets the temperature of the mold temperature adjusting medium to a high temperature that is higher than the temperature of the mold temperature adjusting medium after the blow molding is started and a certain period elapses, and controls the temperature of the mold temperature adjusting medium circulated through the mold in such a way that the surface temperature of the bottle measured immediately after the blow molding is started is approximately to the surface temperature of the bottle measured after the certain period.

5. The aseptic filling machine according to claim 4, wherein let $t1°$ C. be the surface temperature of the body portion of the bottle at the start of the blow molding, and $t2°$ C. be the surface temperature of the body portion of the bottle after the blow molding is started and a specified period elapses, the mold temperature adjusting medium controlling apparatus includes a computation apparatus that raises the temperature of the mold temperature adjusting medium circulated through the body portion mold by $\Delta t°$ C., which is a difference between $t2$ and $t1$, and performs the blow molding of the bottle, feeds back the difference $\Delta t'°$ C. between $t2$ and $t3$ to the mold temperature adjusting medium controlling apparatus when the surface temperature of the body portion of the bottle at the start of the blow molding is $t3°$ C., raises the temperature of the mold temperature adjusting medium circulated through the body portion mold is by $\Delta t'°$ C., and performs the blow molding of the bottle, and repeats the above operation to compute the high temperature $(\Delta t + \Delta t' \ldots)°$ C., which allows $t1$ and $t2$ to be equal to each other.

6. An aseptic filling machine comprising:

a heating apparatus that heats a preform;

a mold formed of a neck portion, a body portion, and a bottom portion that seal the preform to blow-mold the heated preform into a bottle;

a mold surface temperature measuring apparatus that measures a surface temperature of at least the body portion out of surface temperatures of the mold formed of the neck portion, the body portion, and the bottom portion;

a mold temperature adjusting apparatus that includes a mold temperature adjusting medium controlling apparatus that controls a temperature of a mold temperature adjusting medium circulated through the mold formed of the neck portion, the body portion, and the bottom portion and adjusts a temperature of the mold formed of the neck portion, the body portion, and the bottom portion;

a blow-molding apparatus that blow-molds the preform sealed in the mold into the bottle;

a bottle sterilizing apparatus that blasts a gas or mist of a sterilizer or a mixture thereof to the bottle to sterilize the bottle;

a filling apparatus that fills the sterilized bottle with a sterilized content;

a sealing apparatus that seals the bottle filled with the content with a sterilized lid member; and a conveying apparatus that conveys the preform or the bottle from the heating apparatus to the sealing apparatus, wherein when the blow molding is started, the mold temperature adjusting medium controlling apparatus sets the temperature of the mold temperature adjusting medium to a high temperature that is higher than the temperature of the mold temperature adjusting medium after the blow molding is started and a certain period elapses, and controls the temperature of the mold temperature adjusting medium circulated through the mold in such a way that the surface temperature of the mold measured immediately after the blow molding is started is approximately to the surface temperature of the mold measured after the certain period.

* * * * *